(12) United States Patent
Yamakoshi et al.

(10) Patent No.: US 7,452,687 B2
(45) Date of Patent: Nov. 18, 2008

(54) METHOD OF DETECTING MILD IMPAIRED GLUCOSE TOLERANCE OR INSULIN SECRETORY DEFECT

(75) Inventors: Masaru Yamakoshi, Mishima (JP); Takuji Kouzuma, Mishima (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 209 days.

(21) Appl. No.: 10/509,120

(22) PCT Filed: Mar. 27, 2003

(86) PCT No.: PCT/JP03/03771

§ 371 (c)(1),
(2), (4) Date: Nov. 29, 2004

(87) PCT Pub. No.: WO03/083133

PCT Pub. Date: Oct. 9, 2003

(65) Prior Publication Data

US 2005/0214885 A1  Sep. 29, 2005

(30) Foreign Application Priority Data

Mar. 29, 2002   (JP)   ............................. 2002-097121

(51) Int. Cl.
 *C12Q 1/48* (2006.01)
 *C07C 35/16* (2006.01)

(52) U.S. Cl. ........................................ 435/15; 568/833

(58) Field of Classification Search ...................... None
See application file for complete search history.

(56) References Cited

U.S. PATENT DOCUMENTS

| | | | |
|---|---|---|---|
| 5,356,790 A | | 10/1994 | Ueda et al. |
| 5,750,348 A | * | 5/1998 | Larner ........................ 435/7.1 |
| 6,046,018 A | * | 4/2000 | Kozuma et al. ............... 435/26 |
| 6,309,852 B1 | * | 10/2001 | Tazoe et al. .................... 435/26 |

FOREIGN PATENT DOCUMENTS

| | | |
|---|---|---|
| EP | 0 477 001 B1 | 6/1996 |
| EP | 1 008 657 A2 | 6/2000 |
| EP | 1 008 657 A3 | 6/2000 |
| JP | 04-126075 B2 | 4/1992 |
| JP | 04-126099 A | 4/1992 |
| JP | 06-61278 B2 | 8/1994 |
| JP | 2000-298131 A | 10/2000 |
| JP | 2001-190299 A | 7/2001 |
| JP | 2001-190299 A | 7/2001 |
| JP | 2001190299 A * | 7/2001 |
| JP | 3251976 B2 | 1/2002 |
| WO | WO 99/60406 A1 | 11/1999 |

OTHER PUBLICATIONS

Ashizawa et al. An Enzymatic Assay for Myo-Inositol in Tissue Samples; Journal of Biophysical Methods, vol. 44 (2000) pp. 89-94.*
Kennington, A. et al., The New England Journal of Medicine, vol. 323, No. 6, pp. 373-378; (1990).
Suzuki, S. et al., Diabetes Care, vol. 17, No. 12, pp. 1465-1468 (1994).
Research Papers of the Suzuken Memorial Foundation, vol. 17, pp. 249-255; Ikagaku Oyo Kenkyu Zaidan Kenkyu Hokoku (2000), Volume date 1998.
Dolhofer, R. et al., J. Clin.Chem.Clin.Biochem., vol. 25, No. 10, pp. 733-736 (1987).
Kouzuma, T. et al., Clinica Chimica Acta 312, pp. 143-151 (2001).
M. Yamakoshi et al., Clinica Chimica Acta, vol. 328, pp. 163-171, 2003.

* cited by examiner

*Primary Examiner*—Jon P Weber
*Assistant Examiner*—Paul C Martin
(74) *Attorney, Agent, or Firm*—Birch Stewart Kolasch & Birch, LLP

(57) ABSTRACT

It is intended to provide a noninvasive method of conveniently detecting mild impaired glucose tolerance and/or insulin hyposecretion at the early stage with the use of an enzyme. Namely, mild impaired glucose tolerance and/or hyposecretion at the early stage are detected by quantifying myoinositol secreted into the urine before loading glucose and after loading glucose for a definite period of time with the use of a reagent and comparing the increase (or the increase ratio) in the myoinositol content thus measured with a characteristic level which has been preliminarily determined in normal subjects.

12 Claims, 7 Drawing Sheets

METHOD OF DETECTING MILD IMPAIRED GLUCOSE TOLERANCE OR INSULIN SECRETORY DEFECT

FIELD OF THE INVENTION

The present invention relates to a method of examining mild impaired glucose tolerance or insulin secretory defect using a sample such as urine. In addition, the present invention can be applied to a method for predicting or diagnosing a disease that stems from mild impaired glucose tolerance or insulin secretory defect, such as diabetes mellitus, arteriosclerosis, or hypertension; a method of determining effects of prevention of, treatment of, or medical advice on those diseases; and a method of evaluating therapeutic agents for treatment of those diseases.

BACKGROUND OF THE INVENTION

A final goal of diabetic treatment is to prevent the onset of diabetic complications and to inhibit the development thereof. As demonstrated by clinical tests for achieving this goal it is important to find any abnormality and start treatment thereof at the earliest possible stage [e.g., Diabetes Research and Clinical Practice, 28, 103 (1995)].

Further, it is considered effective as a more advanced preventive method to find individuals with prediabetes or at prestage of diabetes, or individuals with mild impaired glucose tolerance or insulin secretory defect, who are not prediabetic at present but are highly likely to develop diabetes or prediabetes in the near future, and give them treatment or advice for exercise and dietary. Clinical tests have been conducted to scientifically demonstrate this [e.g., Diabetes Care, 21, 1720 (1998)]. Therefore, detecting individuals with prediabetes will be important for prevention of diabetes mellitus and also complications thereof. Furthermore, diagnosing individuals with mild impaired glucose tolerance or insulin secretory defect, who are not prediabetic at present but are highly likely to develop diabetes or prediabetes in the near future, is considered most important for purpose of preventing diabetes mellitus at an earlier date.

An example of the diagnostic method for diabetes mellitus is an oral glucose tolerance test. After a 75 gram oral glucose load, a group of individuals with the fasting blood glucose level being less than 110 mg/dl and the 2-hour postload blood glucose level being less than 140 mg/dl is defined as normal glucose tolerance (NGT). In addition, a group of individuals with the fasting blood glucose level being not less than 110 mg/dl but less than 126 mg/dl and the 2-hour postload blood glucose level being less than 140 mg/dl is defined as impaired fasting glycemia (IFG); and a group of individuals with the fasting blood glucose level being less than 126 mg/dl and the 2-hour postload blood glucose level being not less than 140 mg/dl but less than 200 mg/dl is defined as impaired glucose tolerance (IGT); and both groups IFG+IGT are defined as borderline type. A group of individuals with the fasting blood glucose level being not less than 126 mg/dl or the 2-hour postload blood glucose level being not less than 200 mg/dl is defined as diabetes mellitus.

The guideline of the Japan Diabetes Society teaches that among individuals defined as NGT on the basis of only the fasting blood glucose level and the 2-hour postload blood glucose level, those with the 1-hour postload blood glucose levels being 180 mg/dl or more are at higher risk to develop diabetes so that they should be handled as the borderline type.

The term "impaired glucose tolerance" or "glucose tolerance failure" refers to the condition of an increase in blood glucose level caused by insufficient uptake of blood glucose into peripheral tissues such as skeletal muscle, liver, and adipocyte after glucose is introduced into the blood through meals. In addition, the term "mild impaired glucose tolerance" refers to that the increment is slightly higher than that of healthy individuals.

Insulin is a hormone secreted from beta cells of pancreas and acts on skeletal muscle, liver and adipose tissue to lower the blood glucose level. The term "insulin secretory defect" refers to the condition of insufficient insulin secretion to uptake a sufficient amount of blood glucose into peripheral tissues such as skeletal muscle, liver, and adipocyte after glucose is introduced into the blood through meals or the like. Among the insulin secretory defect, the condition of insufficient insulin secretion to uptake the blood glucose into peripheral tissues just after glucose is introduced into the blood is referred to as "impaired early insulin secretion". According to the guideline of the Japan Diabetes Society, the term "impaired early insulin secretion" refers to the condition in which the insulinogenic index I.I is less than 0.4. Insulinogenic index I.I is defined as $\Delta IRI (30\text{-}0)/\Delta PG (30\text{-}0)$ wherein $\Delta IRI (30\text{-}0)$ means between the difference between the blood insulin levels at 30 min after glucose load and before glucose load; and $\Delta PG (30\text{-}0)$ means the difference between the blood glucose levels at 30 min after glucose load and before glucose load.

Assays of blood glucose levels and insulin levels for those diagnoses are invasive procedures that require blood drawing more than once within a short time, giving the subjects considerable pains. Therefore, there is a need for a simple assay with lower invasiveness, which can solve these disadvantages, preferably a noninvasive assay.

On the other hand, the quantitative determination of myo-inositol in a biological sample has been considered useful for the diagnosis of diabetes mellitus and the following reports have been provided.

(a) In diabetes mellitus, there was an increase in the urinary myo-inositol level [Larner J. et al., New Eng. J. Med., 323, 373-378 (1990)].

(b) No difference was found between NGT and the borderline type with respect to the urinary myo-inositol level [Susumu Suzuki, Diabetes Care, Vol. 17, No. 12 (1994) 1465-1468].

(c) The borderline type (IFG, IGT) and diabetes mellitus showed higher urinary myo-inositol level than that of NGT (JP 2001-190299 A).

The above reports (a) and (b) show the results obtained by determining the urinary myo-inositol levels with GC/MS. Nevertheless, the data are problematic in reproducibility and reliability because they varied among different examiners. On the other hand, in the report (c), the results are more precise and reliable than those obtained by GC/MS because they are obtained by determining the urinary myo-inositol level with a high-sensitive myo-inositol assay reagent using an enzyme. In this way, the detection of the group with prediabetes has become possible.

However, the myo-inositol assay reagent used in the report (c) has problems including: (i) an insufficient lower limit of detection because of a narrow measurement range and the need of diluting a sample for determination of various urinary myo-inositol levels; and (ii) insufficient avoidance of effects of coexisting substances in urine, particularly glucose. Therefore, the detection of mild impaired glucose tolerance and insulin secretory defect, which fall within NGT, has been impossible.

Furthermore, if a subject is judged to be NGT on the basis of only blood levels before a 75 g oral glucose load and at 2 hours after the glucose load, such judgment does not reflect the change in blood level from 0 to 2 hours. For example, even individuals (with mild impaired glucose tolerance and insulin secretory defect) who keep a higher blood glucose level from just after the glucose load, and thus are highly likely to develop diabetes or prediabetes in the near future are practically classified in NGT. As used herein, the term "mild impaired glucose tolerance" is classified in NGT, but refers to a slight decrease in glucose tolerance characterized by, when the loading test is carried out and blood samples are collected four times on fasting and at 30 minutes, 1 hour, and 2 hours after the load, (i) an oxyhyperglycemia, i.e., very high blood glucose levels (180 mg/dL or more) at 30 minutes and 1 hour after the load, (ii) a higher blood glucose level than that of healthy individuals at 2 hours after the load although the blood level is less than 140 mg/dL (e.g. not less than 120 mg/dL), (iii) high ΣPG (e.g. 530 mg/dL or more), i.e. the total of blood glucose levels just before 75g oral glucose load and at 30, 60, and 120 minutes after the glucose load Therefore, it can not be anticipated from the public disclosures (a)-(c) to identify the group of individuals who are highly likely to develop diabetes or prediabetes in the near future, for example, individuals with mild impaired glucose tolerance, by determining myo-inositol levels.

In this way, the conventional technology teaches no method of detecting mild impaired glucose tolerance and insulin secretory defect, which keep a higher blood glucose level from just after the glucose load, and thus are highly likely to develop to diabetes or prediabetes in the near future.

SUMMARY OF THE INVENTION

The present invention intends to provide an assay method for simple determination of mild impaired glucose tolerance and/or insulin secretory defect with good reproducibility.

For achieving this object, the present inventors considered that search for any marker for effectively determining mild impaired glucose tolerance and/or insulin secretory defect was advantageous. As a result of concentrated efforts, whereas myo-inositol is conventionally considered to be useful for detection of insulin resistance and prediabetes (borderline type and diabetes mellitus), the present inventors unexpectedly found that myo-inositol is also useful as a marker for effectively detecting mild impaired glucose tolerance or insulin secretory defect Blood serum, plasma, or urine collected from the human body, or a homogenized extract of living tissue are used as a sample. Urine is preferable because it can be non-invasively obtained.

The present inventors continued to develop a high-sensitive quantitative determination assay of myo-inositol and a composition for the assay to provide a simple and cost-effective quantitative determination assay of myo-inositol with a high degree of accuracy (JP 06-61278 B). This enzymatic assay, which does not require any preliminary treatment, opened the way to obtain reliable data of myo-inositol for the first time. Such development of the high-sensitive quantitative determination assay and the composition for the quantitative determination allowed the first success of providing the method of the present invention for examining mild impaired glucose tolerance and/or insulin secretory defect.

Furthermore, after the administration of a given amount of glucose to a subject, urine samples were obtained non-invasively from the subject within a given time period and the myo-inositol levels thereof were determined using the myo-inositol assay reagent as described above. The determination revealed that not only individuals with prediabetes (of borderline type, IFG, IGT) and individuals of diabetes mellitus, but also individuals practically showing mild impaired glucose tolerance in spite of being of NGT and individuals practically showing a decrease in early insulin secretion in spite of being of NGT have higher levels than the characteristic value predetermined from healthy individuals. Therefore, it has been found that the assay reagent of the present invention enables not only the distinction between NGT and non-NGT with progressed impaired glucose tolerance (borderline type, IFG IGT, diabetes) but also the simple, highly reproducible and efficient distinction of individuals practically showing mild impaired glucose tolerance in spite of being of NGT or individuals practically showing a decrease in early insulin secretion in spite of being of NGT from healthy individuals.

In addition, the concentration of myo-inositol in a sample may be very low and some of myo-inositol dehydrogenases used may react weakly with glucose. Thus, the elimination of glucose may be required in advance. A method for the elimination of glucose includes one using extreme chemical stability of myo-inositol and one by modifying glucose using an enzyme as a catalyst. The method using the chemical stability includes, for example, one by heating a sample in the presence of 6 N HCl to allow the acid decomposition of sugars except myo-inositol and recovering myo-inositol remained in the decomposed product; and one by treating a sample with a reducing agent such as sodium borohydride to reduce sugars having carbonyl groups or formyl groups such as glucose except myo-inositol and modifying them to make compounds unreactive with myo-inositol dehydrogenase, i.e. an enzyme for the quantitative myo-inositol assay. The method by modifying glucose using an enzyme as a catalyst includes one by converting glucose in a sample into gluconic acid with glucose oxidase (EC1,1,3,4) and one by converting glucose in a sample into glucose-6-phosphate with hexokinase (EC2,7,1,1).

Various improvements are known in these converting methods. In relation to the method of converting glucose into gluconic acid with glucose oxidase, for example, known is a method to eliminate hydrogen peroxide products by catalase after the reaction with glucose oxidase (JP 63-185397 A).

Furthermore, in relation to the method of converting glucose into glucose-6-phosphate with hexokinase, there are known methods to convert glucose into fructose-1,6-bisphosphate using phosphohexose isomerase and 6-phosphofructokinase to prevent glucose-6-phosphate from being reconverted into glucose through an equilibrium reaction (JP 05-76397 A); to perform the reaction with glucose-6-phosphate dehydrogenase in the presence of an oxidized coenzyme (JP 01-320998 A, JP 03-27299 A); and to perform the reaction with pyruvate kinase in the presence of adenosine diphosphate to prevent the change of adenosine triphosphate level decreasing as glucose is eliminated and thus keep the adenosine triphosphate level constant (JP 02-104298 A).

However, when glucose is eliminated using hexokinase, the enzymatic reaction produces a large amount of ADP in the reaction solution, so that the effect thereof on the enzymatic reaction cannot be ignored. Thus, it is preferable to convert the resulting ADP to a compound that does not affect the reaction.

Thus, the present inventors have considered an effective method using an ADP eliminating agent to convert ADP generated in the reaction solution by the enzymatic reaction to a compound that does not affect the reaction.

Any substances capable of converting ADP to a compound that does not affect the reaction can be used as an ADP eliminating agent Of these, enzymes are preferable and kinases that catalyze conversion of ADP to AMP are more preferable. Kinases are also called phosphokinases or phosphotransferases. Examples of the kinases which catalyze conversion of ADP to AMP include pyrophosphate-glycerol transferase, 6phosphofructokinase, acetate kinase, and ADP-hexokinase.

As a result of keen investigations, the present inventors have found that 6phosophofructokinase and ADP-hexokinase are preferably used as an ADP eliminating agent in the present invention.

When 6phosphofructokinase is used as an ADP eliminating agent in the reaction of eliminating glucose in a sample, ADP is produced along with the conversion of glucose to glucose-6-phosphate using ATP-hexokinase in the presence of ATP and is simultaneously reacted with 6-phosphofructokinase to allow the conversion of ADP to AMP along with the conversion of preadded fructose-6-phosphate to fructose-1,6-bisphosphate.

When ADP-hexokinase is used as an ADP eliminating agent in the reaction of eliminating glucose in a sample, ADP is produced along with the conversion of glucose to glucose-6phosphate using ATP-hexokinase in the presence of ATP and can be converted to AMP.

In addition, it is preferable to perform such reaction in the presence of salts. Examples of the salts include: magnesium salts such as magnesium chloride and magnesium acetate; and potassium salts such as potassium chloride and potassium sulfate. The concentration of salts used is, but not limited to, preferably about 1 to 100 mM.

Any of these compounds produced by the enzymatic modification are not reactive with myo-inositol dehydrogenase, an enzyme for the quantitative myo-inositol determination. The present inventors have found that it is more preferable to previously eliminate glucose by these methods.

Further, the present inventors have found that myo-inositol can be determined more accurately when two kinds of kinases, ATP-hexokinase and ADP-hexokinase, are used simultaneously because the influence of sugars in a sample is reduced. In addition, the present inventors have found that the range of myo-inositol determination can be extended by about 10 times by adjusting thio-NAD level to a final concentration of 0.1 mM or more, preferably 2 to 10 mM. Thus, the present inventors have completed a higher sensitive assay system.

The term "characteristic value" refers to a value determined on the basis of an average of myo-inositol levels in urine samples of healthy subjects selected from those of NGT; standard deviation; and ROC (response operating characteristic) curve. When urine samples are used, the increment in urinary myo-inositol excretion between before the glucose load and at a predetermined time after the glucose load is in the range of 0 to 20 µg/mg creatinine; or 5 to 15 µg/mg creatinine; or more preferably 8 to 12 µg/mg creatinine. In addition, the characteristic value may be changed if a large-scale examination is conducted in the future and the determination is conducted for healthy individuals selected clinically. Furthermore, the characteristic value may also vary depending on the selected populations of race, sex, and age.

BEST MODE FOR CARRYING OUT THE INVENTION

Figure 1:
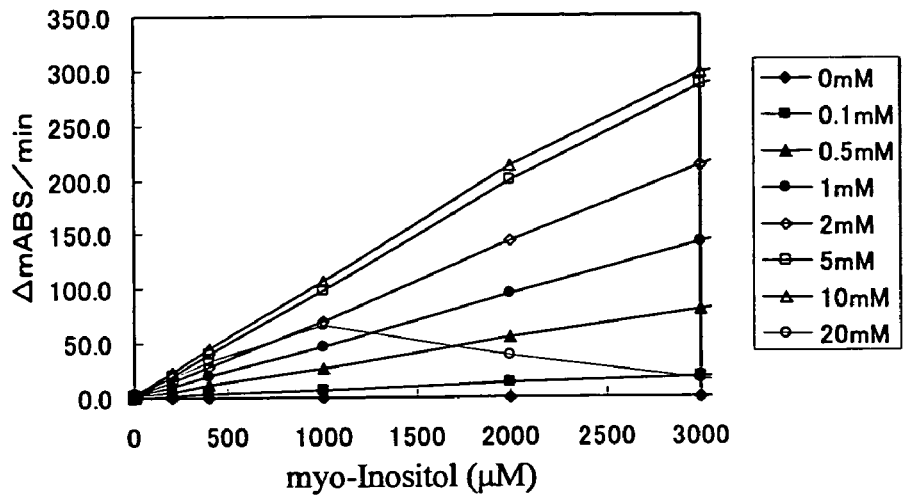
FIG. 1 shows the results of study on thio-NAD levels according to Reference Example 1.

The present invention and preferred embodiments thereof will be described in more detail as below.

According to the present invention, the detection of mild impaired glucose tolerance and insulin secretory defect is carried out by determining the amounts of myo-inositol excreted in urine of a subject before the glucose load and at a predetermined time after the glucose load using the reagent of the present invention; and making a comparison of an increasing amount or increasing rate of myo-inositol between before and after the glucose load with the characteristic value defined in advance for healthy individuals.

The increasing amount is calculated as a difference between the myo-inositol content at a predetermined time after the glucose load and the myo-inositol content before the glucose load, and the increasing rate is calculated as a ratio of the myo-inositol content at a predetermined time after the glucose load to the myo-inositol content before the glucose load.

For the concentration of myo-inositol, an actually determined value may be used, or a relative value with respect to an appropriate standard index may be used for compensating the dilution of urine with drinking water. Preferably, the index is a urinary creatinine level. The subjects include all individuals in addition to those suspected of being lifestyle-related diseases such as diabetes.

Any amounts of glucose loaded and any types of the glucose loading methods may be used. However, preferable is an oral administration of an aqueous 75 g glucose solution as used in a typical glucose load test or a meal ingestion.

Urine samples may be collected before the glucose load and at any times until 6 hours passed just after the glucose load, preferably at 30 minutes to 3 hours after the glucose load. A urine collection period is suitably selected from 30 minutes to 3 hours.

When using urine as a sample, it is collected by a non-invasive method, so that there is no need to select the sampling method, time, and place. For instance, such a sample can be easily prepared by the subject at home, office, school, or the like, and the collected urine sample may be transported directly or in a form of urine-immersed filter paper or other suitable forms, these eliminating the need to be tied to medical institutions or the like. Thus, the present invention provides a prominent method in which, when a filter paper or the like is impregnated with urine, the sample dispatched is extracted by a suitable method and provided to the simple and rapid assay of the present invention and then immediately the results is sent to the subject.

In particular, urinary myo-inositol levels can be monitored as needed while the subject spends everyday life as usual without glucose load. For example, it is possible to grasp the degree of impaired glucose tolerance or the degree of insulin secretory defect using the maximum myo-inositol level or the difference between the maximum myo-inositol level and the minimum myo-inositol level in a day. In addition, monitoring urinary myo-inositol levels as needed allows the subject to reconsider the diet contents and control the amount of exercise to prevent diabetes or the progress thereof while having a regular life.

The methods of monitoring urinary myo-inositol levels include any types of methods capable of detecting myo-inositol, for example, a method using a test paper onto which an enzyme that acts on myo-inositol is fixed and a method of electrochemically detecting myo-inositol using an electrode as a sensor onto which an enzyme acting on myo-inositol is fixed.

In the test paper method, for example, hydrogen peroxide is generated by oxidase and reacted to peroxidase to generate active oxygen, and the active oxygen causes the oxidation of chromogen for coloration, the intensity of which may be observed. The chromogen includes, but not limited to, potassium iodide, tetramethylbenzidine, N-(3-sulfopropyl)-3,3',5,5-'-sodium tetramethylbenzidine, 4-aminoantipyrine, and O-tolidine.

For detecting by means of the sensor, for example, when oxidase is used, hydrogen peroxide generated may be directly measured using an electrode; or the oxidation-reduction current obtained through an electron carrier such as a ferrocene derivative or a quinone derivative or the quantity of the electric current may be measured Likewise, when dehydrogenase is used, the reduced coenzyme may be directly measured using an electrode; or the oxidation-reduction current obtained through an electron carrier or the quantity of the electric current may be measured. Examples are shown in "Biosensor and Quantitative Assay of Substrate Using the Same (Application No. JP 09-263492)" and the like.

In addition, for example, daily monitoring of urinary myo-inositol levels can be more easily carried out by incorporating the above sensor directly into a toilet stool or the like or into a device attached thereto. Such a device may further have functions of memorizing the measurements and of connecting to a terminal of an information processor. In this way, even when the subject stays in a distant place, a medical practitioner or medical institution can make contact with the subject through an electric medium to manage vital data; to give a medical advice; and to examine the degree of impaired glucose tolerance and the degree of insulin secretory defect, leading to review of the diet contents, control of the amount of exercise, improvement of life style, and the medical treatment.

In the case of making quantitative determination of glucose together with myo-inositol in a sample to detect mild impaired glucose tolerance and/or insulin secretory defect, myo-inositol is quantitatively determined preferably by the method of the present invention, while glucose may be quantitatively determined using any conventional methods.

In addition, more precise management can be performed by combining the results of the determination and a doctor's observation. Furthermore, because it is possible to determine the risk to develop diabetes by finding the precondition to diabetes, i.e. prediabetes, and also mild impaired glucose tolerance and insulin secretory defect, which are not prediabetic at present but are highly likely to change to diabetes or prediabetes in the near future, though such finding being impossible by a conventional marker, for example, the risk can be used as an item of examination for life insurance or the like.

For quantitatively determining myo-inositol in a sample, 1 to 500 µL of the sample is added to the composition for myo-inositol quantitative determination to allow a reaction at 37° C. and then the amounts of a coenzyme changed may be directly or indirectly determined for several minutes or several tens of minutes between two time points after the reaction starts, for example, for 1 minute between 3 minutes and 4 minutes after the reaction initiation or for 5 minutes between 3 minutes and 8 minutes. In this case, the myo-inositol content in the sample can be determined by making a comparison with changes in absorbance which are measured for known concentrations of myo-inositol.

The composition (reagent) for the quantitative determination need to contain at least an enzyme that acts on myo-inositol and preferably it further contains a coenzyme.

In addition, a surfactant such as polyoxyethylene octylphenyl ether (OP-10) may be added to the present reagent as appropriate.

Furthermore, the present reagent is used in a form of a liquid product, a freeze-dried product, or a frozen product.

For quantitatively determining myo-inositol in a sample, any types of methods using an enzyme to quantitatively determine myo-inositol may be used. The enzyme to be used in the present invention, which is capable of quantitatively determining myo-inositol, includes any enzymes that act on at least myo-inositol. Of those, however, myo-inositol dehydrogenase is preferable, and myo-inositol dehydrogenase derived from *Flavobaterium* sp. 671 (FERM BP-7323, hereinafter abbreviated as F.sp.671) is most preferable. In addition, preferably, the myo-inositol dehydrogenase to be used has as low as possible or no contamination of substances that adversely affects coenzymes such as thio-NAD and NADH in the reagent, for example, substances having the activity of decomposing coenzymes, such as NADH oxidase.

The strain F.sp.671 is deposited on an international basis with the deposit number of FERM BP-7323 (date of deposit: Oct. 12, 2000) at the National Institute of Bioscience and Human-Technology, Agency of Industrial Science and Technology, The Ministry of International Trade and Industry, located at 1-1-3 Higashi, Tsukuba, Ibaraki, Japan (at present: International Patent Organism Depositary, the National Institute of Advanced Industrial Science and Technology, Independent Administrative Agency, located at Center 6, 1-1-1 Higashi, Tsukuba, Ibaraki, Japan).

For the detection of myo-inositol, any types of methods capable of detecting myo-inositol may be used. The methods include: a method using a visible light coloring reagent, for example, typically yellow coloring with thio-NAD, blue coloring with nitro blue tetrazolium (NBT), or red coloring with 2-(4-iodophenyl)-3-(4-nitrophenyl)-5-phenyl-2H-tetrazolium chloride (INT); a luminescence method; a fluorescence method; a method involving detection of an electric change; and a combination of these methods with amplification techniques.

In addition, using a compact device which can utilize any one of the above methods, the determination of urinary myo-inositol can be carried out non-invasively without restriction on time and place.

The assay for determining the activity of myo-inositol dehydrogenase is as follows:

(1) Activity Assay
<Composition of Reaction Solution>
100 mM Tris buffer (pH 8.5)
20 mM myo-inositol (Sigma Co., Ltd.)
2 mM nicotinamide adenine dinucleotide (NAD) (Oriental Yeast Co., Ltd.)
5 U/ml diaphorase (Asahi Kasei Corporation)
0.025% nitro blue tetrazolium (NBT; Wako Pure Chemical Industries, Ltd.)
1.5% Triton-X100 (Wako Pure Chemical Industries, Ltd.)

One ml of the above reaction solution is added to a small test tube. After the reaction solution is incubated at 37° C. for 5 minutes, 20 µl of an enzyme solution diluted by B times is added thereto and mixed to start the reaction. After the reaction exactly for 5 minutes, 2 ml of 0.1 N HCl is added and mixed to stop the reaction. An absorbance at 550 nm is measured to obtain A1. In addition, the same reaction solution excluding myo-inositol is used to carry out a similar measurement to obtain the absorbance A0. The enzyme activity can be calculated from the following equation.

$$U/ml = [(A1-A0)/18.3] \times [1/5] \times [3.02/0.02] \times B$$

Numerals in the equation represent the following meanings.

18.3: Molar absorption coefficient of NTB
5: Reaction time
3.02: Total volume of reaction solution
0.02: Volume of enzyme solution
B: Dilution factor of enzyme solution The properties of myo-inositol dehydrogenase derived from the strain F.sp.671 are as follows:

(2) Enzyme Action

This enzyme produces inosose and a reduced coenzyme in the presence of at least myo-inositol and a coenzyme. The coenzyme includes nicotinamide adenine dinucleotides (hereinafter abbreviated as NADs) such as nicotinamide adenine dinucleotide (NAD), acetylpyridine adenine dinucleotide (acetyl-NAD), nicotinamide hypoxanthine dinucleotide (deamino-NAD), pyridine aldehyde adenine dinucleotide (aldehyde-NAD), nicotinamide adenine dinucleotide phosphate (NADP), thio-nicotinamide adenine dinucleotide (thio-NAD), and thio-nicotinamide adenine dinucleotide phosphate (thio-NADP).

Table 1 shows the ratio of relative activities on use of each coenzyme (as 100% when NAD is used as a coenzyme). The relative activities were determined with the coenzyme changed according to the following method.

Relative Activity Assay
<Composition of Reaction Solution>
Buffer: 100 mM glycine buffer (pH 10.0)
Substrate: 20 mM myo-inositol (Sigma, Co., Ltd.)
Coenzyme: 2 mM (NAD, thio-NAD, NADP, thio NADP; Oriental Yeast Co., Ltd.)

One ml of the above reaction solution is added to a quartz cell. Then, the quartz cell is placed in a spectrophotometer adjusted at a temperature of 37° C. The cell is incubated for 5 minutes or more and then 20 µl of an enzyme solution of about 1.0 U/ml is added thereto and mixed. The initial velocity is obtained from an absorbance change per minute at a wavelength peculiar to each reduced coenzyme. The initial velocity obtained with each coenzyme is compared with the initial velocity (100%) obtained using NAD as a coenzyme to provide the relative activity.

TABLE 1

Relative activity ratio for each coenzyme used

| Name of bacterial strain<br>Coenzyme | F.sp.671<br>myo-Inositol |
|---|---|
| NAD | 100% |
| NADP | 8% |
| Thio-NAD | 29% |
| Thio-NADP | 0% |

(3) Substrate Specificity

According to the relative activity assay described above, the measurement was performed using the same concentration of D-chiro-inositol, D-mannose, D-fructose, D-galactose, mannitol, epi-inositol, or scyllo-inositol in place of the substrate in the reaction solution. Table 2 shows the enzyme activity for each substrate referring to the initial velocity of the reaction to myo-inositol as 100%. It is revealed that the enzyme derived from the strain F.sp.671 is dehydrogenase having high specificity to myo-inositol.

The substrates used include D-mannose, D-fructose, D-galactose, mannitol, D-chiro-inositol (as above: Wako Pure Chemical Industries, Ltd.), myo-inositol, epi-inositol, and scyllo-inositol (as above: Sigma, Co., Ltd.).

TABLE 2

Substrate specificity

| Name of bacterial strain<br>Coenzyme | F.sp.671<br>NAD |
|---|---|
| myo-Inositol | 100% |
| chiro-Inositol | 18% |
| scyllo-Inositol | less than 1% |
| epi-Inositol | 2% |
| Galactose | less than 1% |
| Fructose | less than 1% |
| Mannose | less than 1% |
| Mannitol | 0% |

(4) Optimum pH

Following the relative activity assay described above, the measurement was performed using each of 100 mM tris buffer (pH 7.0-9.0) and 100 mM glycine buffer (pH 9.0-11.0) in place of 100 mM of pH 10.0 glycine buffer in the reaction solution. The measurement showed that the optimum pH was about 11.0 (substrate: myo-inositol).

(5) Molecular Weight

Used were TSK gel G300SW (0.75 Φ×600 mm), eluent: 50 mM phosphate buffer (pH 7.5) +0.2 M $Na_2SO_4$+0.05% $NaN_3$, and a molecular marker set of Oriental Yeast Co., Ltd. (Japan), a chromatography apparatus made by Shimadzu Corporation (Japan). For the detection, the absorbance at UV 280 nm and the activity of each fraction were measured. myo-Inositol was used as a substrate in the activity measurement, revealing the molecular weight of 40,000±10,000.

(6) Heat Stability

The enzyme showed almost 100% remaining activity after treatment at 40° C. for 15 minutes. The enzyme solution of about 5 U/ml was subjected to heat treatment for 15 minutes. The remaining activity was measured using the enzyme activity assay described above. In the activity measurement, myo-inositol was used as a substrate.

(7) Km value

Using the relative activity assay described above, the concentration of myo-inositol and the concentrations of NAD and thio-NAD were changed to determine Km values respectively. Using the activity assay described above, the substrate concentration was changed to calculate the Km value.

Km value for substrate myo-Inositol: 1.7±0.2 mM

Km value for coenzyme

NAD: 0.04±0.01 mM

Thio NAD: 4.5±1 mM

For the quantitative determination of myo-inositol with higher sensitivity, the enzymatic cycling method can be used. An example of the enzymatic cycling method is illustrated in the following equation.

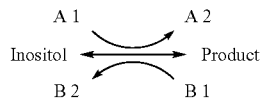

In the equation, A1 represents NAD(P) or thio-NAD(P); A2 represents a reduced form of A1; B1 represents reduced NAD(P) when A1 is thio-NAD(P) or reduced thio-NADP) when A1 is NAD(P); and B2 represents an oxidized product of B1. As used herein, NAD(P) represents nicotinamide adenine dinucleotide and nicotinamide adenine dinucleotide phosphate.

For the solution composition of the quantitative reaction of myo-inositol using the enzymatic cycling, two or more of coenzymes are appropriately selected in view of Km values of respective coenzymes of myo-inositol dehydrogenase, and the like, and subsequently the pH condition is adjusted between the optimal pH values of forward reaction/reverse reaction to make an efficient progress in the enzymatic cycling. The amounts of A1 and B1 should be excess over the myo-inositol content in a sample and also excess over Km values of myo-inositol dehydrogenase for A1 and B1.

When using, for instance, myo-inositol dehydrogenase derived from F.sp.671, the Km values for NAD and thio-NAD are 0.04 mM and 4.5 mM, respectively. For the cycling reaction, thio-NAD and NADH may be selected as coenzymes. The concentrations of A1 and B1 are preferably 0.02 mM to 2 M, particularly preferably 0.05 to 100 mM. The amount of myo-inositol dehydrogenase is preferably 1 to 1000 U/mL, particularly preferably 1 to 100 U/mL. The amounts can be suitably selected on the basis of type and amount of the test sample, the myo-inositol content in the sample to be assayed, and the like; but other amounts may be also allowed.

When hexokinase is used as an enzyme for eliminating sugars presented in a sample, any hexokinase capable of catalyzing the reaction from glucose to glucose-6-phosphate may be used, including hexokinase derived from *Bacillus* sp. Preferable hexokinase is one having excellent heat stability. The hexokinase having excellent heat stability can be obtained by the method described in "Stable Hexokinase and Production Method Thereof" (JP 2000-078982 A).

Because ADP generated together with glucose-6-phosphate has some inhibitory effect on the reaction in the enzymatic cycling method, the present inventors successfully have used ADP-dependent hexokinase simultaneously with hexokinase to improve substantially the elimination of glucose without any influence on the reaction of myo-inositol dehydrogenase.

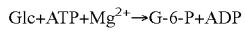

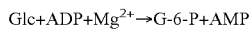

ATP: Adenosine-5'-triphosphate

ADP: Adenosine-5'-diphosphate

AMP: Adenosine-5'-monophosphate

The assay of hexokinase activity is conducted as follows.

<Composition of Reaction Solution>

50 mM Tris buffer (pH 8.5) (Sigma, Co., Ltd.)

20 mM glucose (Wako Pure Chemical Industries, Ltd.)

4 mM ATP (Oriental Yeast Co., Ltd.)

5 U/mL glucose-6-phosphate dehydrogenase (Toyobo Co., Ltd.)

1 mM NADP (Oriental Yeast Co., Ltd.)

10 mM magnesium chloride (Wako Pure Chemical Industries, Ltd.)

Solution for dissolving and diluting the enzyme: 50 mM Tris buffer (pH 8.5)

One mL of the above reaction solution is added to a quartz cell with 1-cm optical path length, and incubated at 37° C. for 5 minutes. Then, 20 µL of the enzyme solution, which is diluted B times, is added thereto and mixed to start the reaction. The absorbance at 340 nm is measured from the initiation of the reaction to obtain the absorbance change A1 per minute, which shows a linear reaction. A blind test is also conducted in a similar reaction to obtain the absorbance change A0 per minute, except that 50 µL of the solution for dissolving and diluting the enzyme is added instead of the enzyme solution. The enzyme activity is calculated from the following equation.

$$U/ml = [(A1-A0)/6.22] \times [1.02/0.02] \times B$$

Numerals in the equation represent the following meanings.

6.22: Millimolar extinction coefficient of NADPH at 340 nm 1.02: Total volume of reaction solution (mL)

0.02: Volume of enzyme solution used in the reaction (mL)

B: Dilution factor of enzyme solution

The assay of ADP-dependent hexokinase activity is conducted as follows.

<Composition of Reaction Solution>

50 mM Tris buffer (pH 7.5)

20 mM glucose solution (Wako Pure Chemical Industries, Ltd)

2 mM ADP solution (pH 7.0) (Oriental Yeast Co., Ltd.)

5 U/mL glucose-6-phosphate dehydrogenase (Asahi Kasei Corporation)

1 mM NADP solution (Oriental Yeast Co., Ltd)

2 mM magnesium chloride solution (Wako Pure Chemical Industries, Ltd)

Solution for dissolving and diluting the enzyme: 10 mM Tris buffer (pH 7.5)

Three mL of the above reaction solution is added to a small test tube, and incubated at 37° C. for 5 minutes. Then, 50 µL of the enzyme solution, which is diluted by B times, is added thereto and mixed to start the reaction. The absorbance at 340 nm is measured from the initiation of the reaction to obtain the absorbance change A1 per minute, which shows a linear reaction. A blind test is also conducted in a similar reaction to obtain the absorbance change A0 per minute, except that 50 µL of the solution for dissolving and diluting the enzyme is added instead of the enzyme solution. The enzyme activity is calculated from the following equation.

$$U/ml = [(A1-A0)/6.22] \times [3.05/0.05] \times B$$

Numerals in the equation represent the following meanings.

6.22: Millimolar extinction coefficient of NADPH at 340 nm
3.05: Total volume of reaction solution (mL)
0.05: Volume of enzyme solution used in the reaction (mL)
B: Dilution factor of enzyme solution The amount of hexokinase is preferably 1 to 1,000 u/mL, particularly preferably 1 to 100 u/mL. The amount of ADP-dependent hexokinase is preferably 1 to 1,000 u/ml, particularly preferably 1 to 100 u/mL. The amounts can be appropriately selected depending on type and amount of the test sample, and other amounts can be also used.

In addition, for the determination of urinary myo-inositol over a wide range of its concentration with good reproducibility, an enzymatic cycling reaction should be effectively performed. As a result of intensive examination on concentrations and ratio of thio-NAD and NADH, two coenzymes to be used in the enzymatic cycling reaction, the present inventors have found that the thio-NAD level is preferably 0.01 mM or more, particularly preferably 2 to 10 mM in a final concentration and the ratio of NADH/thio-NAD is preferably 0.01 to 0.5, particularly preferably 0.01 to 0.1. However, the amounts can be appropriately selected according to type and amount of the test sample, and other amounts may be applied.

EXAMPLES

The examples of the present invention and reference examples will be described in detail, but the present invention is not limited thereto.

Reference Example 1

Study on thio-NAD Levels

1) Reagents
<R-1>
5 mM MES (2-Morpholinoethanesulfonic acid) (pH 6.0)
0 to 40 mM thio-NAD (Oriental Yeast Co., Ltd.)
<R-2; Reagent for myo-Inositol Quantitative Determination>
200 mM Bicine (pH 9.0)
0.3 mM NADH (Oriental Yeast Co., Ltd.)
25 u/mL myo-inositol dehydrogenase (Asahi Kasei Corporation)

2) Method
The measurement device used was Autoanalyzer 7170S (Hitachi Chemical Co., Ltd.). To 3 μL of myo-inositol solution at concentrations of 0 to 3,000 μM, 180 μL of R-1 reagent was added and incubated at 37° C. for 4.8 minutes, followed by the addition of 180 μL of R-2 reagent to start the reaction. Absorbances at 405 nm were measured at 5.4 and 7.8 minutes after the reaction initiation, and then the difference therebetween was obtained. An increasing rate of absorbance per minute (ΔmABS/min) was calculated and the sensitivity was then investigated with respect to the standard solution.

3) Results
The results are shown in FIG. 1. As shown in FIG. 1, using thio-NAD at final concentrations of 0.1 to 10 mM, the linearity of the calibration curve was observed over myo-inositol concentrations of 0 to 3,000 μm. In addition, it has been found that the final concentration of thio-NAD is preferably 2 to 10 mM to enhance the sensitivity of myo-inositol detection.

Reference Example 2

Study on Buffers in Reagents for myo-Inositol Quantitative Determination

1) Reagents
<R-1>
5 mM MES (pH 6.0)
5 mM thio-NAD (Oriental Yeast Co., Ltd.)
<R-2; Reagent for myo-Inositol Quantitative Determination>
100 mM Buffer (pH 8.8)
0.5 mM NADH (Oriental Yeast Co., Ltd)
10 u/mL myo-inositol dehydrogenase (Asahi Kasei Corporation)

2) Method
R-2 reagents for myo-inositol quantitative determination were prepared following the above shown composition with a buffer being selected from:
Tris (Tris(hydroxymethyl)aminomethane),
Tricine (N-Tris(hydroxymethyl)methylglycine),
Bicine (N,N-Bis(hydroxyethyl)glycine),
TAPS (N-Tris(hydroxymethyl)methyl-3-aminopropanesulfonic acid),
TEA (Triethanolamine),
CHES (2-Cyclohexylamino)ethanesulfonic acid), and
AMPSO(3-((1,1-Dimethyl-2-hydroxy-ethyl)amino)-2-hydroxypropanesulfonic acid).

The measurement device used was Autoanalyzer 7170S (Hitachi Chemical Co., Ltd.). To 15 μL of the standard 100-μM myo-inositol solution prepared in advance, 180 μL of R-1 reagent was added and incubated at 37° C. for 4.8 minutes, followed by the addition of 60 μL of R-2 reagent to start the reaction. Absorbances at 405 nm were measured at 5.4 and 7.8 minutes after the reaction initiation, and then the difference therebetween was obtained. An increasing rate of absorbance per minute (ΔmABS/min) was calculated and the sensitivity was then investigated with respect to the standard solution. The stability of each R-2 reagent was investigated by an acceleration test wherein only R-2 reagent was stored in an incubator at 30° C. for 20 days and then the same test as described above was conducted on the 7th, 12th, and 20th days.

Figure 2:
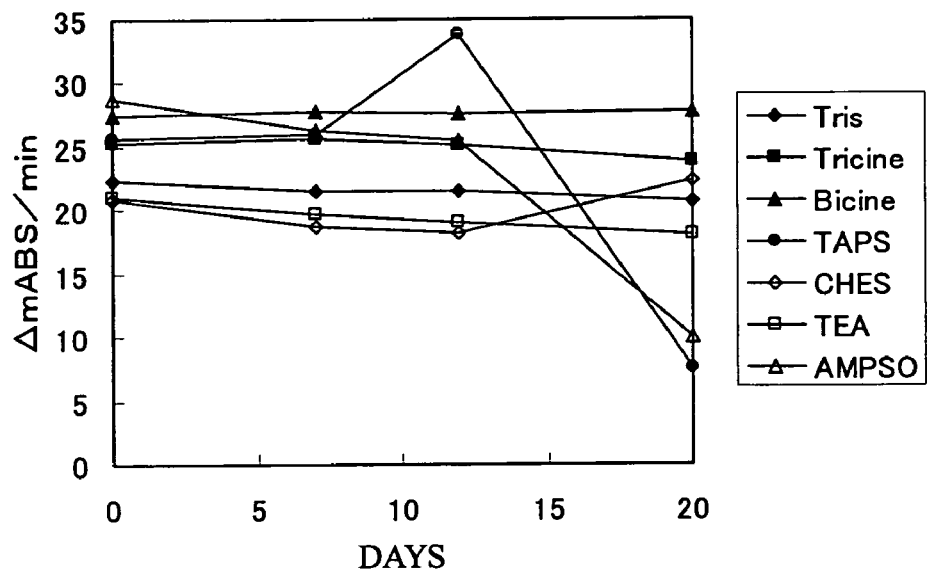
FIG. 2 shows the results of stability test of myo-inositol assay reagents according to Reference Example 2.

3) Results
The results are shown in FIG. 2. The buffers showing stable sensitivity in comparison to the standard solution were Tris, Tricine, Bicine and TEA; and the buffer having the most stable sensitivity was Bicine.

Reference Example 3

Study on ADP-Hexokinase

1) Reagents
<R-1>
5 mM MES (pH 6.0)
5 mM $MgCl_2$ (Wako Pure Chemical Industries, Ltd.)
8 mM ATP (Oriental Yeast Co., Ltd.)
10 mM thio-NAD (Oriental Yeast Co., Ltd.)

10 u/mL ATP-hexolinase (Asahi Kasei Corporation)
0 to 4 u/mL ADP-hexokinase (Asahi Kasei Corporation)
<R-2; Reagent for myo-Inositol Quantitative Determination>
200 mM Bicine (pH 9.0)
0.3 mM NADH (Oriental Yeast Co., Ltd.)
25 u/mL myo-inositol dehydrogenase (Asahi Kasei Corporation)

2) Method

The measurement device used was Autoanalyzer 7170S (Hitachi Chemical Co., Ltd.). Samples were prepared by mixing 100 μL of 2,000 μM myo-inositol solution and 1 mL of 0 to 10 g/dL glucose solution. To 3 μL of each sample, 180 μL of R-1 reagent was added and incubated at 37° C. for 4.8 minutes, followed by the addition of 180 μL of R-2 reagent to start the reaction. Absorbances at 405 nm were measured at 5.4 and 7.8 minutes after the reaction initiation, and then the difference therebetween was obtained. An increasing rate of absorbance per minute (ΔmABS/min) was calculated and the sensitivity was then investigated for respective samples.

3) Results

Figure 3:
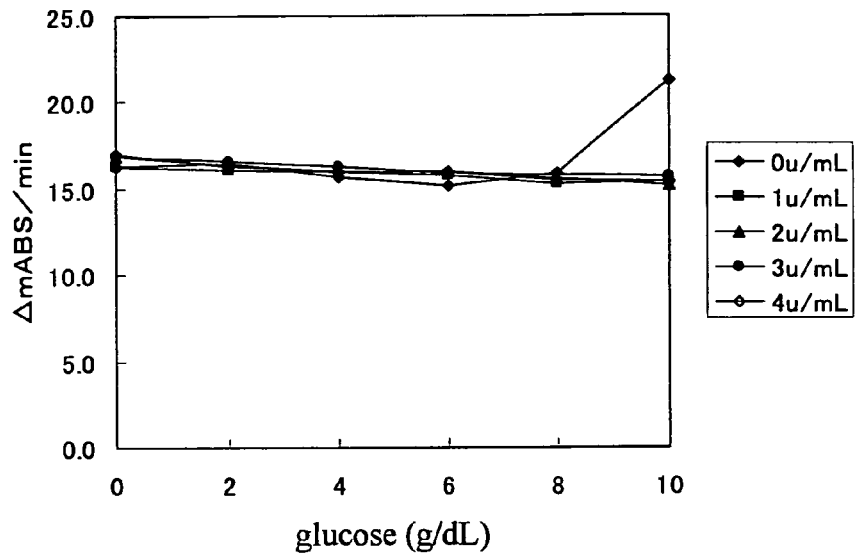
FIG. 3 shows the effects of ADP-hexokinase according to Reference Example 3.

The results are shown in FIG. 3. As is evident from FIG. 3, when using ATP-hexolinase alone, the increasing glucose level, e.g. of 10 g/dL causes an influence on the sensitivity. In contrast, when using ATP-hexolinase together with ADP-hexolinase, the increasing glucose level has no influence on the sensitivity. This indicates that glucose in a sample can be eliminated by simultaneous reaction with ATP-hexolinase and ADP-hexokinase; and thus myo-inositol level can be determined more accurately.

Reference Example 4 myo-Inositol Quantitative Determination with High Sensitivity using Enzyme

1) Reagents
Reagent for myo-Inositol Assay
<R-1; Glucose Eliminating Reagent>
5 mM MES (pH 6.0)
0.05% $NaN_3$ (Wako Pure Chemical Industries, Ltd.)
0.05% OP-10 (Nippon Chemicals)
5 mM $MgCl_2$ (Wako Pure Chemical Industries, Ltd.)
8 mM ATP (Oriental Yeast Co., Ltd.)
10 mM thio-NAD (Oriental Yeast Co., Ltd.)
10 u/mL ATP-hexolinase (Asahi Kasei Corporation)
4 u/mL ADP-hexokinase (Asahi Kasei Corporation)
<R-2; Reagent for myo-Inositol Quantitative Determination>
200 mM Bicine (pH 9.0)
0.05% $NaN_3$ (Wako Pure Chemical Industries, Ltd.)
40 mM $KHCO_3$ (Wako Pure Chemical Industries, Ltd.)
0.3 mM NADH (Oriental Yeast Co., Ltd.)
25 u/mL myo-inositol dehydrogenase (Asahi Kasei Corporation)

2) Method

The measurement device used was Autoanalyzer 7170S (Hitachi Chemical Co., Ltd.). To 3 μL of the myo-inositol solution prepared in advance, 180 μL of the glucose eliminating reagent was added and incubated at 37° C. for 4.8 minutes for the glucose eliminating reaction, and then 180 μL of the reagent for myo-inositol quantitative determination was added thereto to start the reaction. Absorbances at 405 nm were measured at 5.4 and 7.8 minutes after the reaction initiation, and then the difference therebetween was obtained. An increasing rate of absorbance per minute (ΔmABS/min) was calculated.

3) Results

Figure 4:
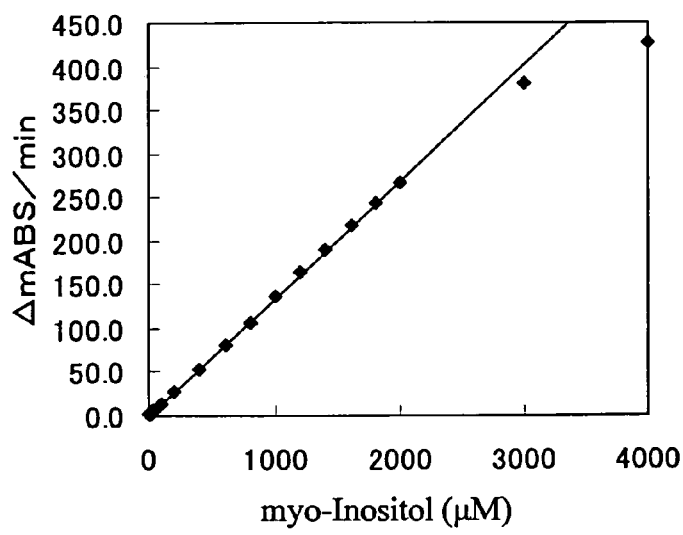
FIG. 4 shows the calibration curve for myo-inositol levels according to Reference Example 4.

The results are shown in FIG. 4. As shown in FIG. 4, the present assay reagent allowed quantitative determination of myo-inositol in a simple way. The measurement range of myo-inositol was 0 to 2,000 μM and the lower limit of detection was 10 μM when the lower limit of detection was defined as the minimum concentration, which does not overlap "the mean of ΔmABS/min+2×standard deviation" obtained by multiple measurements of 0 mM myo-inositol.

Example 1

Detection of Mild Impaired Glucose Tolerance by Determination of Urinary myo-Inositol 1) Subjects:

One hundred and twelve subjects were examined by the standard 75 g oral glucose load test. Blood samples were collected just before the glucose load, and at 30, 60, 120, and 180 minutes after the glucose load to determine levels of blood glucose and insulin. Simultaneously, urine samples were collected just before the glucose load, and at 60, 120, and 180 minutes after the glucose load to determine levels of myo-inositol, urinary glucose, and creatinine.

2) Reagents and Assays:

Blood glucose: Electrode method (Kyoto Daiichi Kagaku Corporation: GA-1160)
Insulin: RIA2 Antibody method
myo-Inositol Assay Reagent: the same as that of Example 4
Urinary glucose: Electrode method (Kyoto Daiichi Kagaku Corporation: GA-1160)
Creatinine: Creatinine-HA Test Wako (Wako Pure Chemical Industries, Ltd.)

3) Method:

ΣPG, the total of blood glucose levels just before 75 g oral glucose load, and at 30, 60, and 120 minutes after the glucose load, was used as an index of glucose tolerance. myo-Inositol level and creatinine level in respective urine samples just before the 75 g oral glucose load, and at 30, 60, and 120 minutes after the glucose load were determined to calculate the myo-inositol amount to the amount of urinary creatinine excreted (myo-inositol/creatine). In addition, Δ myo-inositol content [(myo-inositol content at 60 min−myo-inositol content before load)/2]+[(myo-inositol content at 120 min−myo-inositol content before load)/2] was used as an index of myo-inositol level between before and after the glucose load The relationship between ΣPG and Δ myo-inositol content was investigated.

Figure 5:
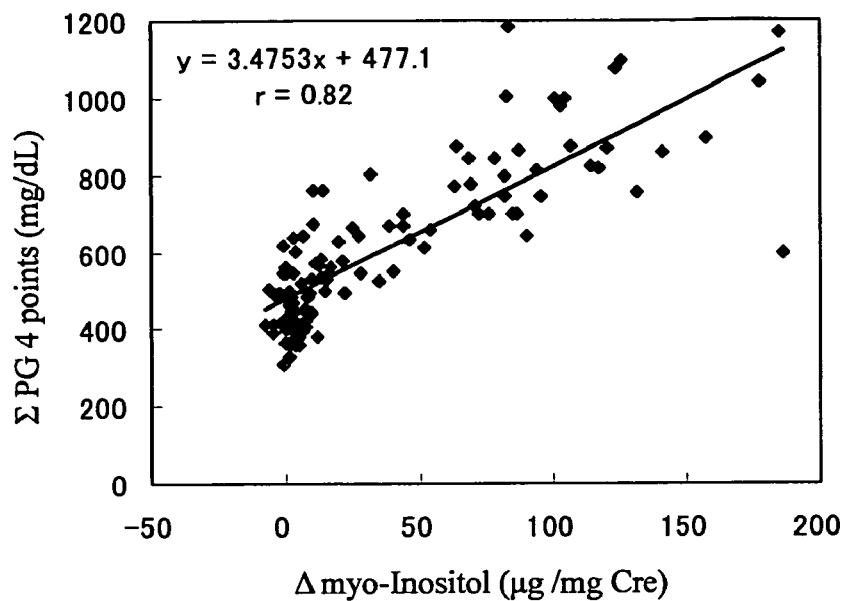
FIG. 5 shows the relationship between myo-inositol level and ΣPG according to Example 1.

4) Results:

The results are shown in Table 3 and FIG. 5. As shown in FIG. 5, ΣPG and Δ myo-inositol content showed a very good correlation. Higher ΣPG indicates that blood glucose levels are kept higher after the glucose load, and thus the presence of impaired glucose tolerance. In addition, for example, if the characteristic value of Δ myo-inositol is set as 10 μg/mg Cre (creatinine), an effective detection can be made for cases having mild impaired glucose tolerance with ΣPG level of about 530 mg/dL.

TABLE 3

| | | Blood glucose (mg/dL) | | | | | | Insulin (μU/mL) | | | | | LI | Urinary myo-inositol (μg/mg Cre) | | | | | Δmyo- | Urinary Glucose (g/dL) | | | | Δmyo- | ΣPG | ΔIRI/ΔPG |
|---|---|---|---|---|---|---|---|---|---|---|---|---|---|---|---|---|---|---|---|---|---|---|---|---|---|---|
| | | 0 min. | 30 | 60 | 120 | 180 | ΣPG | 0 min. | 30 | 60 | 120 | 180 | | 0 min. | 60 | 120 | 180 | Δmyo | 0 min. | 60 | 120 | 180 | Inositol | | |
| 1 | Normal | 89 | 150 | 161 | 135 | 94 | 535 | 5 | 23 | 23 | 22 | 13 | 0.30 | 13 | 24 | 33 | 26 | 15 | 0.03 | 0.02 | 0.02 | 0.01 | 15 | 535 | 0.30 |
| 2 | Normal | 105 | 160 | 153 | 65 | 107 | 483 | 6 | 59 | 40 | 24 | 22 | 0.96 | 23 | 24 | 40 | 26 | 9 | 0.02 | 0.01 | 0.01 | 0.01 | 9 | 483 | 0.96 |
| 3 | Normal | 102 | 119 | 158 | 121 | 76 | 500 | 2 | 26 | 47 | 20 | 11 | 1.41 | 11 | 12 | 13 | 13 | -1 | 0.01 | 0.07 | 0.03 | 0.02 | -1 | 500 | 1.41 |
| 4 | Normal | 85 | 170 | 143 | 98 | 85 | 496 | 5 | 41 | 76 | 21 | 14 | 0.42 | 46 | 60 | 51 | 43 | 9 | 0 | 0.03 | 0.01 | 0.01 | 9 | 496 | 0.42 |
| 5 | Normal | 106 | 164 | 162 | 115 | 83 | 547 | 5 | 17 | 19 | 20 | 8 | 0.21 | 13 | 13 | 19 | 15 | 3 | 0.02 | 0.03 | 0.03 | 0.02 | 3 | 547 | 0.21 |
| 6 | Normal | 96 | 125 | 139 | 134 | 125 | 494 | 5 | 10 | 24 | 25 | 16 | 0.17 | 26 | 38 | 69 | 68 | 23 | 0.01 | 0.03 | 0.03 | 0.03 | 23 | 494 | 0.17 |
| 7 | Normal | 92 | 130 | 139 | 90 | 78 | 451 | 5 | 16 | 13 | 19 | 11 | 0.29 | 13 | 24 | 32 | 29 | 7 | 0.01 | 0.03 | 0.03 | 0.01 | 7 | 451 | 0.29 |
| 8 | Normal | 101 | 144 | 135 | 108 | 107 | 488 | 7 | 37 | 27 | 36 | 34 | 0.70 | 24 | 17 | 23 | 22 | -4 | 0.02 | 0.03 | 0.01 | 0.01 | -4 | 488 | 0.70 |
| 9 | Normal | 87 | 161 | 172 | 109 | 78 | 529 | 5 | 25 | 21 | 17 | 4 | 0.30 | 25 | 35 | 46 | 44 | 16 | 0.01 | 0.03 | 0 | 0.03 | 16 | 529 | 0.30 |
| 10 | Normal | 106 | 175 | 167 | 133 | 60 | 581 | 13 | 83 | 124 | 107 | 14 | 1.01 | 17 | 26 | 35 | 25 | 14 | 0.02 | 0 | 0 | 0.01 | 14 | 581 | 1.01 |
| 11 | Normal | 106 | 158 | 129 | 128 | 72 | 521 | 12 | 63 | 50 | 73 | 11 | 0.98 | 20 | 16 | 14 | 14 | 6 | 0.01 | 0 | 0.01 | 0 | 6 | 521 | 0.98 |
| 12 | Normal | 101 | 137 | 101 | 83 | 82 | 422 | 11 | 87 | 86 | 25 | 10 | 2.11 | 7 | 12 | 20 | 13 | 7 | 0.01 | 0.01 | 0 | 0 | 7 | 422 | 2.11 |
| 13 | Normal | 98 | 129 | 81 | 101 | 97 | 409 | 7 | 49 | 10 | 18 | 11 | 1.35 | 9 | 23 | 18 | 20 | 8 | 0.01 | 0.01 | 0.01 | 0.01 | 8 | 409 | 1.35 |
| 14 | Normal | 92 | 127 | 123 | 85 | 70 | 427 | 9 | 39 | 25 | 18 | 8 | 0.86 | 9 | 12 | 11 | 12 | 0 | 0.02 | 0.01 | 0 | 0 | 0 | 427 | 0.86 |
| 15 | Normal | 95 | 132 | 103 | 102 | 69 | 432 | 8 | 39 | 30 | 28 | 12 | 0.84 | 13 | 11 | 11 | 11 | 3 | 0.01 | 0.03 | 0.01 | 0.01 | 3 | 432 | 0.84 |
| 16 | Normal | 106 | 167 | 107 | 102 | 85 | 482 | 10 | 75 | 32 | 21 | 9 | 1.07 | 11 | 10 | 12 | 11 | 2 | 0.03 | 0.03 | 0.02 | 0.02 | 2 | 482 | 1.07 |
| 17 | Normal | 88 | 121 | 138 | 100 | 79 | 447 | 6 | 18 | 32 | 15 | 5 | 0.36 | 9 | 10 | 15 | 17 | 4 | 0.01 | 0.02 | 0.01 | 0.01 | 4 | 447 | 0.36 |
| 18 | Normal | 97 | 130 | 88 | 103 | 102 | 418 | 5 | 28 | 18 | 14 | 8 | 0.70 | 14 | 13 | 11 | 11 | -2 | 0.02 | 0.01 | 0 | 0 | -2 | 418 | 0.70 |
| 19 | Normal | 99 | 151 | 114 | 105 | 106 | 469 | 7 | 5 | 8 | 24 | 16 | 0.00 | 10 | 10 | 12 | 18 | 3 | 0 | 0.01 | 0 | 0.01 | 3 | 469 | 0.00 |
| 20 | Normal | 102 | 148 | 178 | 127 | 89 | 553 | 8 | 62 | 59 | 38 | 20 | 1.17 | 41 | 70 | 92 | 47 | 40 | 0.02 | 0.24 | 0.4 | 0.03 | 40 | 553 | 1.17 |
| 21 | Normal | 89 | 108 | 120 | 92 | 102 | 409 | 10 | 51 | 65 | 21 | 37 | 2.16 | 35 | 34 | 40 | 31 | 2 | 0.01 | 0.01 | 0.01 | 0.01 | 2 | 409 | 2.16 |
| 22 | Normal | 91 | 144 | 153 | 105 | 72 | 493 | 8 | 75 | 67 | 38 | 7 | 1.25 | 28 | 26 | 25 | 17 | -2 | 0.01 | 0.03 | 0.02 | 0.01 | -2 | 493 | 1.25 |
| 23 | Normal | 101 | 154 | 148 | 91 | 73 | 494 | 5 | 26 | 36 | 14 | 5 | 0.40 | 7 | 8 | 8 | 9 | -1 | 0.02 | 0.02 | 0.02 | 0 | -1 | 494 | 0.40 |
| 24 | Normal | 96 | 148 | 177 | 124 | 52 | 545 | 10 | 29 | 59 | 67 | 10 | 0.37 | 11 | 11 | 11 | 11 | 0 | 0.01 | 0.03 | 0.02 | 0.02 | 0 | 545 | 0.37 |
| 25 | Normal | 95 | 168 | 98 | 84 | 76 | 445 | 6 | 78 | 20 | 16 | 4 | 0.99 | 24 | 34 | 30 | 31 | 8 | 0.01 | 0.02 | 0.01 | 0 | 8 | 445 | 0.99 |
| 26 | Normal | 89 | 147 | 93 | 84 | 55 | 413 | 5 | 26 | 23 | 21 | 4 | 0.36 | 7 | 9 | 14 | 14 | 5 | 0.02 | 0.01 | 0 | 0 | 5 | 413 | 0.36 |
| 27 | Normal | 90 | 129 | 93 | 101 | 81 | 413 | 7 | 36 | 14 | 17 | 6 | 0.74 | 25 | 22 | 20 | 19 | -4 | 0 | 0.01 | 0 | 0.01 | -4 | 413 | 0.74 |
| 28 | Normal | 75 | 96 | 75 | 84 | 60 | 330 | 3 | 37 | 12 | 13 | 4 | 1.62 | 11 | 13 | 13 | 14 | 2 | 0.03 | 0.01 | 0.01 | 0.02 | 2 | 330 | 1.62 |
| 29 | Normal | 92 | 127 | 87 | 83 | 69 | 389 | 5 | 32 | 25 | 11 | 5 | 0.91 | 25 | 21 | 20 | 18 | -4 | 0.03 | 0.01 | 0 | 0.01 | -4 | 389 | 0.91 |
| 30 | Normal | 83 | 109 | 107 | 101 | 78 | 400 | 4 | 32 | 27 | 26 | 12 | 0.88 | 16 | 15 | 17 | 14 | -4 | 0 | 0 | 0 | 0 | -4 | 400 | 0.88 |
| 31 | Normal | 100 | 123 | 71 | 89 | 79 | 383 | 7 | 32 | 33 | 13 | 3 | 1.09 | 5 | 18 | 13 | 10 | 5 | 0.03 | 0 | 0 | 0 | 5 | 383 | 1.09 |
| 32 | Normal | 96 | 110 | 75 | 87 | 82 | 370 | 6 | 46 | 20 | 18 | 7 | 2.86 | 15 | 13 | 12 | 12 | 2 | 0.01 | 0.01 | 0.02 | 0.02 | 2 | 370 | 2.86 |
| 33 | Normal | 91 | 108 | 82 | 80 | 82 | 361 | 7 | 16 | 17 | 19 | 8 | 0.53 | 10 | 8 | 8 | 15 | 4 | 0.02 | 0.01 | 0.01 | 0 | 4 | 361 | 0.53 |
| 34 | Normal | 91 | 140 | 152 | 99 | 59 | 482 | 3 | 2 | 5 | 7 | 3 | -0.02 | 7 | 11 | 8 | 7 | 1 | 0.01 | 0.01 | 0.02 | 0.01 | 1 | 482 | -0.02 |
| 35 | Normal | 79 | 119 | 120 | 89 | 60 | 407 | 4 | 9 | 7 | 5 | 2 | 0.13 | 10 | 12 | 15 | 14 | 4 | 0.02 | 0.01 | 0.01 | 0 | 4 | 407 | 0.13 |
| 36 | Normal | 100 | 151 | 148 | 139 | 100 | 538 | 10 | 41 | 45 | 49 | 27 | 0.61 | 18 | 26 | 38 | 36 | 14 | 0.01 | 0.03 | 0.03 | 0.01 | 14 | 538 | 0.61 |
| 37 | Normal | 96 | 119 | 110 | 85 | 63 | 410 | 5 | 38 | 34 | 18 | 5 | 1.43 | 20 | 22 | 28 | 29 | 5 | 0.01 | 0.01 | 0.01 | 0 | 5 | 410 | 1.43 |
| 38 | Normal | 99 | 145 | 149 | 109 | 63 | 502 | 9 | 21 | 31 | 17 | 7 | 0.26 | 23 | 36 | 40 | 32 | 15 | 0.02 | 0.02 | 0.02 | 0.01 | 15 | 502 | 0.26 |
| 39 | Normal | 85 | 98 | 101 | 82 | 50 | 366 | 4 | 14 | | | 4 | 0.77 | 8 | 9 | 8 | 9 | 0 | 0.01 | 0.01 | 0.01 | 0 | 0 | 366 | 0.77 |
| 40 | Normal | 89 | 114 | 87 | 91 | 63 | 381 | 7 | 9 | 10 | 15 | 3 | 0.08 | 27 | 35 | 44 | 44 | 12 | 0 | 0.02 | 0.01 | 0.01 | 12 | 381 | 0.08 |
| 41 | Normal | 95 | 169 | 175 | 109 | 59 | 548 | 11 | 35 | 46 | 29 | 7 | 0.32 | 9 | 8 | 9 | 9 | 0 | 0.01 | 0.01 | 0.01 | 0.01 | 0 | 548 | 0.32 |
| 42 | Normal | 76 | 78 | 66 | 90 | 84 | 310 | 2 | 7 | 4 | 10 | 5 | 2.50 | 8 | 10 | 9 | 8 | -1 | 0.01 | 0.03 | 0.02 | 0.01 | -1 | 310 | 2.50 |
| 43 | Normal | 100 | 124 | 92 | 87 | 65 | 403 | 8 | 51 | 29 | 18 | 5 | 1.79 | 8 | 7 | 9 | 12 | -1 | 0.01 | 0 | 0 | 0 | -1 | 403 | 1.79 |
| 44 | Normal | 95 | 138 | 117 | 91 | 67 | 441 | 7 | 26 | 44 | 27 | 6 | 0.44 | 10 | 17 | 23 | 26 | 10 | 0.02 | 0 | 0.01 | 0 | 10 | 441 | 0.44 |
| 45 | Normal | 89 | 106 | 85 | 82 | 79 | 362 | 6 | 79 | 32 | 16 | 4 | 4.29 | 7 | 8 | 9 | 12 | 2 | 0.02 | 0.01 | 0 | 0 | 2 | 362 | 4.29 |
| 46 | Normal | 103 | 192 | 153 | 96 | 80 | 544 | 9 | 33 | 44 | 20 | 5 | 0.27 | 18 | 56 | 38 | 28 | 28 | 0.02 | 0.77 | 0.06 | 0.01 | 28 | 544 | 0.27 |
| 47 | Normal | 87 | 131 | 123 | 109 | 69 | 450 | 6 | 42 | 36 | 24 | 4 | 0.82 | 7 | 10 | 10 | 9 | 3 | 0.01 | 0.01 | 0.01 | 0.01 | 3 | 450 | 0.82 |

TABLE 3-continued

| | | Blood glucose (mg/dL) | | | | | | Insulin (μU/mL) | | | | | | LI | Urinary myo-inositol (μg/mg Cre) | | | | Δmyo- | Urinary Glucose (g/dL) | | | | Δmyo- | ΣPG | ΔIRI/ΔPG |
|---|---|---|---|---|---|---|---|---|---|---|---|---|---|---|---|---|---|---|---|---|---|---|---|---|---|---|
| | | 0 min. | 30 | 60 | 120 | 180 | ΣPG | 0 min. | 30 | 60 | 120 | 180 | | | 0 min. | 60 | 120 | 180 | Δmyo | 0 min. | 60 | 120 | 180 | Inositol | | |
| 48 | Normal | 99 | 126 | 104 | 83 | 66 | 412 | 10 | 47 | 9 | 15 | 5 | 1.37 | 27 | 18 | 21 | 18 | −7 | 0 | 0.02 | 0 | 0.01 | −7 | 412 | 1.37 |
| 49 | Normal | 88 | 106 | 86 | 85 | 89 | 363 | 3 | 22 | 18 | 17 | 8 | 0.95 | 14 | 20 | 19 | 20 | 5 | 0 | 0 | 0 | 0 | 5 | 363 | 0.95 |
| 50 | Normal | 84 | 131 | 89 | 89 | 80 | 393 | 6 | 40 | 24 | 12 | 10 | 0.72 | 10 | 15 | 17 | 16 | 5 | 0.03 | 0 | 0 | 0 | 5 | 393 | 0.72 |
| 51 | Normal | 85 | 116 | 99 | 110 | 83 | 410 | 6 | 17 | 17 | 18 | 9 | 0.35 | 13 | 13 | 12 | 11 | −1 | 0.03 | 0.02 | 0.02 | 0 | −1 | 410 | 0.35 |
| 52 | Normal | 87 | 122 | 89 | 96 | 88 | 394 | 6 | 27 | 30 | 35 | 13 | 0.60 | 13 | 16 | 20 | 24 | 7 | 0.02 | 0.02 | 0.01 | 0 | 7 | 394 | 0.60 |
| 53 | Normal | 90 | 147 | 112 | 116 | 52 | 465 | 6 | 72 | 53 | 50 | 4 | 1.16 | 11 | 14 | 17 | 13 | 2 | 0 | 0 | 0 | 0 | 2 | 465 | 1.16 |
| 54 | Normal | 92 | 187 | 186 | 133 | 49 | 598 | 3 | 17 | 25 | 27 | 13 | 0.15 | 17 | 16 | 22 | 26 | 186 | 0 | 0.23 | 0.15 | 0.03 | 186 | 598 | 0.15 |
| 55 | Normal | 99 | 146 | 181 | 138 | 137 | 559 | 5 | 19 | 16 | 15 | 4 | 0.30 | 368 | 487 | 623 | 395 | 1 | 0 | 0 | 0.01 | 0 | 1 | 559 | 0.30 |
| 56 | Normal | 99 | 160 | 206 | 133 | 68 | 603 | 11 | 30 | 49 | 72 | 13 | 0.31 | 4 | 4 | 4 | 3 | 4 | 0.03 | 0.04 | 0.05 | 0 | 4 | 603 | 0.31 |
| 57 | Normal | 107 | 151 | 189 | 115 | 44 | 562 | 6 | 16 | 44 | 38 | 18 | 0.23 | 7 | 20 | 14 | 10 | 18 | 0 | 0.03 | 0.03 | 0 | 18 | 562 | 0.23 |
| 58 | Normal | 105 | 194 | 234 | 110 | 81 | 643 | 5 | 17 | 40 | 23 | 7 | 0.13 | 13 | 32 | 42 | 30 | 28 | 0.02 | 0.04 | 0.05 | 0.02 | 28 | 643 | 0.13 |
| 59 | Normal | 89 | 167 | 187 | 130 | 108 | 573 | 22 | 133 | 142 | 104 | 11 | 1.42 | 24 | 34 | 72 | 29 | 12 | 0 | 0.02 | 0.13 | 0 | 12 | 573 | 1.42 |
| 60 | Normal | 117 | 165 | 154 | 90 | 80 | 526 | 8 | 37 | 108 | 27 | 79 | 0.60 | 26 | 46 | 41 | 27 | 35 | 0.01 | 0.06 | 0.01 | 0 | 35 | 526 | 0.60 |
| 61 | IFG | 115 | 174 | 206 | 136 | 65 | 631 | 4 | 8 | 19 | 20 | 11 | 0.07 | 24 | 33 | 72 | 45 | 46 | 0.01 | 0.23 | 0.08 | 0 | 46 | 631 | 0.07 |
| 62 | IFG | 117 | 204 | 220 | 103 | 152 | 644 | 7 | 31 | 37 | 33 | 4 | 0.28 | 12 | 33 | 84 | 25 | 90 | 0.01 | 0.61 | 0.55 | 0.12 | 90 | 644 | 0.28 |
| 63 | IFG | 110 | 185 | 240 | 127 | 120 | 662 | 8 | 15 | 28 | 15 | 16 | 0.12 | 37 | 113 | 140 | 56 | 26 | 0.01 | 0.05 | 1.04 | 0.03 | 26 | 662 | 0.12 |
| 64 | IFG | 111 | 183 | 200 | 83 | 75 | 577 | 4 | 16 | 22 | 12 | 8 | 0.17 | 17 | 26 | 59 | 29 | 22 | 0 | 0.1 | 0.12 | 0.01 | 22 | 577 | 0.17 |
| 65 | IFG | 110 | 153 | 60 | 88 | 82 | 411 | 5 | 44 | 53 | 18 | 4 | 0.91 | 16 | 26 | 48 | 28 | 4 | 0.01 | 0.01 | 0.17 | 0.01 | 4 | 411 | 0.91 |
| 66 | IFG | 117 | 236 | 192 | 101 | 71 | 646 | 24 | 196 | 100 | 48 | 15 | 1.45 | 13 | 15 | 19 | 19 | 7 | 0 | 0.03 | 0.02 | 0 | 7 | 646 | 1.45 |
| 67 | IFG | 111 | 166 | 167 | 124 | 70 | 568 | 12 | 53 | 55 | 40 | 17 | 0.75 | 12 | 19 | 21 | 13 | 13 | 0.01 | 0.02 | 0.03 | 0.01 | 13 | 568 | 0.75 |
| 68 | IFG | 113 | 204 | 229 | 115 | 58 | 661 | 5 | 20 | 47 | 44 | 8 | 0.16 | 9 | 22 | 96 | 42 | 54 | 0.01 | 0.89 | 0.53 | 0.03 | 54 | 661 | 0.16 |
| 69 | IFG | 111 | 192 | 237 | 161 | 63 | 701 | 10 | 18 | 26 | 48 | 12 | 0.10 | 49 | 67 | 146 | 94 | 85 | 0.02 | 0.37 | 1.31 | 0.41 | 85 | 701 | 0.10 |
| 70 | IGT | 104 | 153 | 130 | 141 | 141 | 528 | 7 | 28 | 24 | 17 | 9 | 0.43 | 22 | 22 | 29 | 56 | 10 | 0.01 | 0.02 | 0.01 | 0.01 | 10 | 528 | 0.43 |
| 71 | IGT | 113 | 195 | 224 | 170 | 147 | 702 | 7 | 19 | 37 | 48 | 16 | 0.15 | 15 | 114 | 185 | 176 | 86 | 0.01 | 0.67 | 0.38 | 0.14 | 86 | 702 | 0.15 |
| 72 | IGT | 98 | 158 | 213 | 143 | 48 | 612 | 5 | 14 | 72 | 33 | 31 | 0.15 | 63 | 72 | 149 | 75 | 52 | 0.03 | 0.19 | 1.16 | 0.17 | 52 | 612 | 0.15 |
| 73 | IGT | 95 | 119 | 147 | 142 | 73 | 503 | 4 | 20 | 44 | 29 | 5 | 0.63 | 59 | 31 | 36 | 40 | −6 | 0.01 | 0.01 | 0.03 | 0.01 | −6 | 503 | 0.63 |
| 74 | IGT | 103 | 187 | 217 | 164 | 111 | 671 | 5 | 18 | 30 | 35 | 6 | 0.14 | 40 | 55 | 74 | 27 | 4 | 0.01 | 0.02 | 0.02 | 0.01 | 4 | 671 | 0.14 |
| 75 | IGT | 123 | 196 | 232 | 150 | 158 | 701 | 6 | 30 | 60 | 67 | 11 | 0.37 | 21 | 88 | 119 | 88 | 44 | 0.05 | 0.95 | 0.53 | 0.66 | 44 | 701 | 0.37 |
| 76 | IGT | 108 | 150 | 192 | 168 | 124 | 618 | 3 | 17 | 22 | 32 | 56 | 0.33 | 33 | 14 | 15 | 13 | 72 | 0.01 | 0.02 | 0.02 | 0.02 | 72 | 618 | 0.33 |
| 77 | IGT | 114 | 178 | 204 | 172 | 136 | 668 | 4 | 10 | 13 | 17 | 26 | 0.09 | 14 | 71 | 89 | 80 | 0 | 0.03 | 0.04 | 0.13 | 0.03 | 0 | 668 | 0.09 |
| 78 | IGT | 108 | 211 | 214 | 167 | 69 | 700 | 6 | 36 | 50 | 41 | 10 | 0.29 | 27 | 44 | 116 | 49 | 39 | 0.01 | 0.22 | 0.43 | 0.03 | 39 | 700 | 0.29 |
| 79 | IGT | 97 | 211 | 256 | 196 | 117 | 760 | 4 | 20 | 28 | 34 | 16 | 0.12 | 16 | 83 | 112 | 90 | 76 | 0.02 | 0.06 | 0.05 | 0.01 | 76 | 760 | 0.12 |
| 80 | IGT | 123 | 218 | 244 | 160 | 83 | 745 | 2 | 11 | 13 | 21 | 4 | 0.09 | 36 | 86 | 29 | 26 | 15 | 0.03 | 1.41 | 1.54 | 0.02 | 15 | 745 | 0.09 |
| 81 | IGT | 100 | 161 | 204 | 173 | 101 | 638 | 7 | 9 | 12 | 14 | 12 | 0.03 | 16 | 50 | 150 | 27 | 95 | 0.02 | 0.02 | 0.03 | 0.02 | 95 | 638 | 0.03 |
| 82 | IGT | 110 | 219 | 240 | 186 | 100 | 755 | 6 | 15 | 21 | 31 | 13 | 0.08 | 32 | 117 | 210 | 178 | 3 | 0.02 | 3.12 | 4.13 | 1.44 | 3 | 755 | 0.08 |
| 83 | Diabetic | 127 | 206 | 250 | 178 | 125 | 761 | 8 | 21 | 25 | 37 | 21 | 0.16 | 15 | 14 | 36 | 27 | 131 | 0.02 | 0.03 | 0.14 | 0.08 | 131 | 761 | 0.16 |
| 84 | Diabetic | 128 | 249 | 279 | 214 | 89 | 870 | 6 | 22 | 43 | 46 | 15 | 0.13 | 32 | 119 | 221 | 144 | 11 | 0.03 | 1.6 | 1.33 | 0.31 | 11 | 870 | 0.13 |
| 85 | Diabetic | 151 | 228 | 263 | 256 | 166 | 898 | 5 | 12 | 13 | 16 | 7 | 0.09 | 50 | 152 | 262 | 208 | 120 | 0.03 | 0.85 | 2.33 | 1.02 | 120 | 898 | 0.09 |
| 86 | Diabetic | 170 | 278 | 326 | 322 | 197 | 1096 | 5 | 7 | 8 | 11 | 9 | 0.02 | 50 | 146 | 232 | 225 | 157 | 0.01 | 1.33 | 3.46 | 2.75 | 157 | 1096 | 0.02 |
| 87 | Diabetic | 204 | 281 | 337 | 363 | 286 | 1185 | 12 | 15 | 19 | 26 | 28 | 0.04 | 64 | 146 | 232 | 151 | 125 | 0.05 | 3.42 | 7.25 | 7.25 | 125 | 1185 | 0.04 |
| 88 | Diabetic | 112 | 209 | 262 | 237 | 91 | 820 | 4 | 11 | 18 | 15 | 15 | 0.06 | 21 | 63 | 145 | 112 | 83 | 0.01 | 1.17 | 0.98 | 0.16 | 83 | 820 | 0.06 |
| 89 | Diabetic | 129 | 232 | 288 | 225 | 122 | 874 | 4 | 11 | 20 | 10 | 10 | 0.07 | 33 | 106 | 195 | 80 | 117 | 0.03 | 2.82 | 5.89 | 1.16 | 117 | 874 | 0.07 |
| 90 | Diabetic | 106 | 171 | 253 | 243 | 115 | 773 | 8 | 9 | 20 | 32 | 15 | 0.08 | 14 | 71 | 170 | 106 | 106 | 0.03 | 0.99 | 5.11 | 1.96 | 106 | 773 | 0.08 |
| 91 | Diabetic | 110 | 203 | 232 | 201 | 105 | 746 | 4 | 41 | 43 | 46 | 14 | 0.38 | 27 | 44 | 135 | 79 | 63 | 0.02 | 1.57 | 1.92 | 1.25 | 63 | 746 | 0.38 |
| 92 | Diabetic | 139 | 225 | 286 | 326 | 245 | 976 | 8 | 5 | 8 | 10 | 8 | 0.01 | 16 | 83 | 112 | 90 | 82 | 0.02 | 2.71 | 6.43 | 8.73 | 82 | 976 | 0.01 |
| 93 | Diabetic | 118 | 232 | 285 | 232 | 114 | 865 | 4 | 15 | 20 | 31 | 15 | 0.07 | 36 | 86 | 191 | 62 | 103 | 0.05 | 1.09 | 0.73 | 0.11 | 103 | 865 | 0.07 |
| 94 | Diabetic | 132 | 220 | 329 | 318 | 223 | 999 | 7 | 49 | 80 | 105 | 74 | 0.22 | 38 | 40 | 155 | 167 | 87 | 0.02 | 0.12 | 0.4 | 0.61 | 87 | 999 | 0.22 |
| 95 | Diabetic | 102 | 178 | 250 | 250 | 122 | 780 | 2 | 9 | 13 | 36 | 16 | 0.09 | 18 | 26 | 148 | 91 | 69 | 0.03 | 0.08 | 3.31 | 1.16 | 69 | 780 | 0.09 |

TABLE 3-continued

| | | Blood glucose (mg/dL) | | | | | Insulin (μU/mL) | | | | | | Urinary myo-inositol (μg/mg Cre) | | | | Δmyo | Urinary Glucose (g/dL) | | | | ΣPG | ΔIRI/ΔPG |
|---|---|---|---|---|---|---|---|---|---|---|---|---|---|---|---|---|---|---|---|---|---|---|---|
| | | 0 min. | 30 | 60 | 120 | 180 | ΣPG | 0 min. | 30 | 60 | 120 | 180 | LI | 0 min. | 60 | 120 | 180 | Inositol | 0 min. | 60 | 120 | 180 | | |
| 96 | Diabetic | 173 | 239 | 352 | 311 | 201 | 1075 | 9 | 7 | 23 | 36 | 20 | −0.03 | 49 | 108 | 236 | 227 | 123 | 0.04 | 2.21 | 6.46 | 4.85 | 1075 | −0.03 |
| 97 | Diabetic | 152 | 236 | 224 | 264 | 263 | 876 | 6 | 17 | 14 | 12 | 11 | 0.13 | 40 | 62 | 146 | 167 | 64 | 0.01 | 0.15 | 0.18 | 0.11 | 876 | 0.13 |
| 98 | Diabetic | 166 | 252 | 306 | 274 | 205 | 998 | 3 | 11 | 17 | 20 | 10 | 0.09 | 15 | 71 | 161 | 114 | 100 | 0.01 | 1.38 | 4.5 | 1.68 | 998 | 0.09 |
| 99 | Diabetic | 101 | 249 | 373 | 444 | 342 | 1167 | 3 | 5 | 7 | 6 | 5 | 0.01 | 37 | 154 | 290 | 301 | 185 | 0.02 | 3.44 | 2.45 | 2.1 | 1167 | 0.01 |
| 100 | Diabetic | 162 | 239 | 314 | 299 | 162 | 1004 | 7 | 11 | 33 | 31 | 12 | 0.05 | 33 | 56 | 174 | 127 | 83 | 0.03 | 0.36 | 3.29 | 2.23 | 1004 | 0.05 |
| 101 | Diabetic | 141 | 208 | 261 | 189 | 138 | 799 | 3 | 4 | 7 | 11 | 8 | 0.01 | 28 | 66 | 154 | 67 | 82 | 0.02 | 0.12 | 0.66 | 0.02 | 799 | 0.01 |
| 102 | Diabetic | 136 | 236 | 262 | 225 | 209 | 859 | 7 | 14 | 18 | 20 | 10 | 0.07 | 73 | 160 | 268 | 181 | 141 | 0.01 | 0.92 | 1.76 | 0.53 | 859 | 0.07 |
| 103 | Diabetic | 101 | 128 | 193 | 206 | 138 | 628 | 6 | 15 | 25 | 58 | 46 | 0.33 | 13 | 19 | 46 | 28 | 20 | 0.02 | 0 | 0.02 | 0.02 | 628 | 0.33 |
| 104 | Diabetic | 110 | 198 | 241 | 257 | 151 | 806 | 5 | 24 | 32 | 55 | 31 | 0.22 | 45 | 55 | 99 | 118 | 32 | 0.01 | 0.15 | 1.3 | 1.61 | 806 | 0.22 |
| 105 | Diabetic | 253 | 253 | 346 | 291 | 158 | 1042 | 5 | 19 | 44 | 16 | 23 | 0.09 | 99 | 183 | 371 | 280 | 178 | 0.11 | 3.02 | 3.32 | 3.2 | 1042 | 0.09 |
| 106 | Diabetic | 129 | 239 | 202 | 130 | 86 | 700 | 10 | 39 | 65 | 24 | 6 | 0.31 | 24 | 69 | 67 | 40 | 44 | 0.03 | 1.76 | 0.59 | 0.12 | 700 | 0.31 |
| 107 | Diabetic | 112 | 200 | 250 | 283 | 246 | 845 | 5 | 11 | 15 | 29 | 27 | 0.06 | 33 | 66 | 157 | 178 | 78 | 0.01 | 0.42 | 1.62 | 2.5 | 845 | 0.06 |
| 108 | Diabetic | 111 | 198 | 251 | 254 | 171 | 814 | 6 | 17 | 20 | 32 | 21 | 0.14 | 17 | 43 | 180 | 167 | 94 | 0.02 | 0.48 | 0.99 | 0.84 | 814 | 0.14 |
| 109 | Diabetic | 137 | 198 | 258 | 232 | 141 | 825 | 5 | 11 | 30 | 21 | 8 | 0.10 | 27 | 105 | 177 | 138 | 114 | 0.08 | 3.88 | 6.04 | 3.78 | 825 | 0.10 |
| 110 | Diabetic | 134 | 201 | 276 | 233 | 151 | 844 | 5 | 13 | 19 | 20 | 11 | 0.12 | 22 | 43 | 138 | 85 | 68 | 0.02 | 0.65 | 4.88 | 2.69 | 844 | 0.12 |
| 111 | Diabetic | 111 | 169 | 240 | 201 | 101 | 721 | 4 | 12 | 28 | 28 | 10 | 0.14 | 27 | 63 | 132 | 90 | 70 | 0.01 | 0.43 | 1.44 | 0.1 | 721 | 0.14 |
| 112 | Diabetic | 136 | 201 | 200 | 137 | 141 | 674 | 7 | 8 | 10 | 20 | 13 | 0.02 | 26 | 35 | 38 | 31 | 11 | 0.01 | 0.01 | 0 | 0 | 674 | 0.02 |

Example 2

Figure 6:
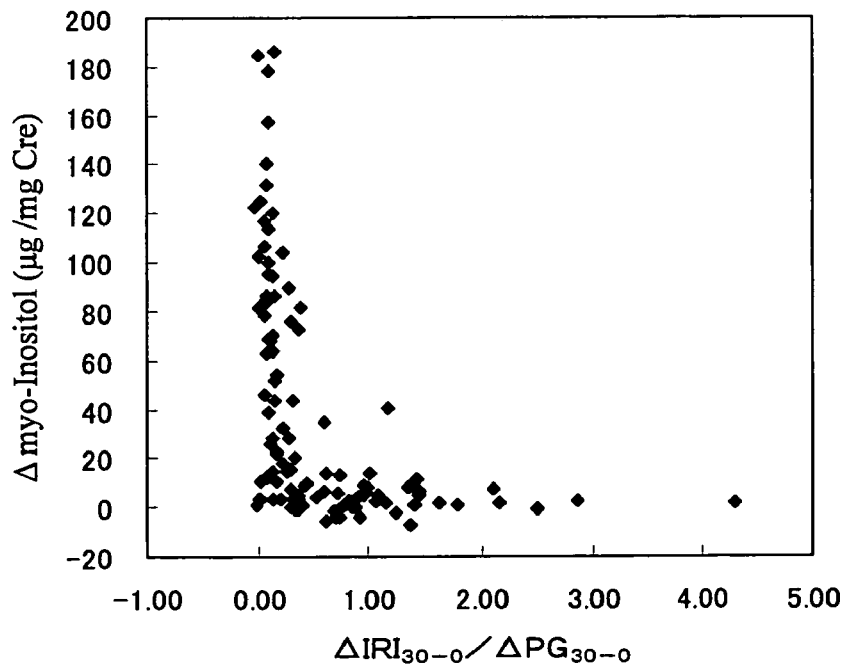
FIG. 6 shows the relationship between inositol level and insulinogenic index according to Example 2.

Detection of Impaired Early insulin Secretion by Determination of Urinary myo-Inositol 1) Subjects:
The same as those of Example 1.
2) Reagents and Assays:
The same as those of Example 1.
3) Method:
myo-Inositol levels and creatinine levels in each urine sample just before the 75 g oral glucose load, and at 60 and 120 minutes after the glucose load were determined, and then the myo-inositol amount to the amount of urinary creatinine excreted (myo-inositol/creatinine) was obtained. In addition, Δ myo-inositol content [(myo-inositol content at 60 min–myo-inositol content before load)/2]+[(myo-inositol content at 120 min–myo-inositol content before load)/2] was used as the index of myo-inositol level between before and after the glucose load. The relationship between the insulinogenic index (I.I) and Δ myo-inositol content was investigated.
4) Results:
The results are shown in FIG. 6. As shown in FIG. 6, the relationship between the insulinogenic index and Δ myo-inositol content was found. In a large percentage of cases where the Δ myo-inositol content was 15 μg/mg Cre or more, the insulinogenic index showed less than 0.4. According to the guideline of the Japan Diabetes Society, the insulinogenic index of less than 0.4 can judge the presence of impaired early insulin secretion. As is evident from FIG. 6, if the characteristic value of Δ myo-inositol is 15 μg/mg Cre, an effective detection can be made for cases showing the insulinogenic index of less than 0.4, or having impaired early insulin secretion.

Example 3

Detection of Mild Impaired Glucose Tolerance by Determination of Urinary myo-Inositol and Urinary Glucose 1) Subjects:
The same as those of Example 1.
2) Reagents and Assays:
The same as those of Example 1.
3) Method:
myo-Inositol levels and creatinine levels in each urine sample just before the 75 g oral glucose load, and at 60 and 120 minutes after the glucose load were determined. Then, the myo-inositol content to the amount of urinary creatinine excreted (myo-inositol/creatinine) was obtained. At the same time, urinary glucose levels were also obtained. Δ myo-inositol content [(myo-inositol content at 60 min–myo-inositol content before load)/2]+[(myo-inositol content at 120 min–myo-inositol content before load)/2] was used as the index of myo-inositol level between before and after the glucose load.
4) Results
The case showing Δ myo-inositol content of 10 μg/mg Cre or more was referred to as plus (+), while the other case was referred to as minus (−). Likewise for the urinary glucose, the case showing an urinary glucose level of 50 mg/dL or more at 2 hours after glucose load was referred to as "+", while the other case was referred to as "−". ΣPG values calculated in Example 5 were used.

Out of 112 subjects tested, 52 subjects were in the group of Δ myo-inositol (−) and urinary glucose (−), 12 subjects were in the group of Δ myo-inositol (+) and urinary glucose (−), and 48 subjects were in the group of Δ myo-inositol (+) and urinary glucose (+). Nobody corresponded to the group of Δ myo-inositol (−) and urinary glucose (+). The respective ΣPG values of the group of Δ myo-inositol (−) and urinary glucose (−), the group of Δ myo-inositol (+) and urinary glucose (−), and the group of Δ myo-inositol (+) and urinary glucose (+) were compared with one another.

Figure 7:
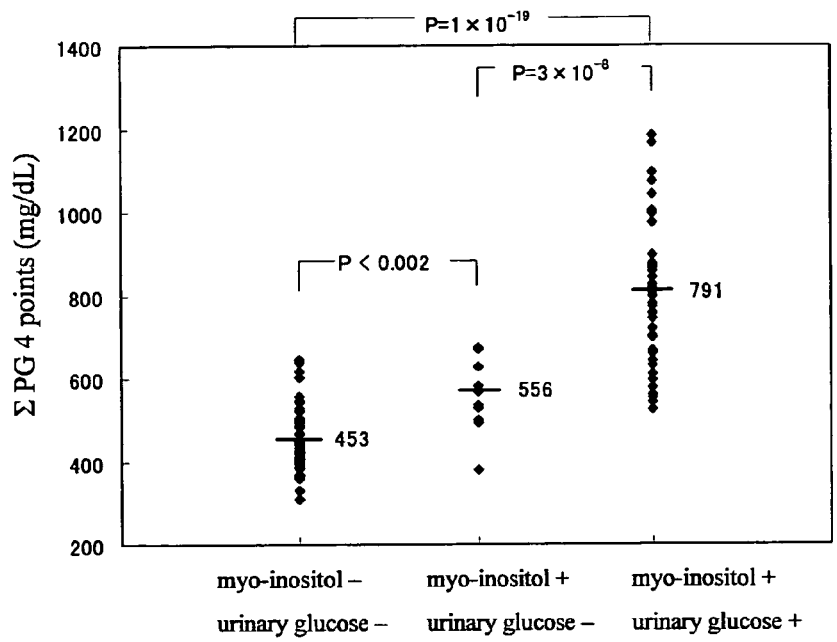
FIG. 7 shows the relationship between each group and ΣPG according to Example 3.

The results are shown in FIG. 7. As shown in FIG. 7, the mean and standard deviation of ΣPG values of the group of Δ myo-inositol (−) and urinary glucose (−) were 453 mg/dL and 76.6 mg/dL, respectively. The mean and standard deviation of ΣPG values of the group of Δ myo-inositol (+) and urinary glucose (−) were 556 mg/dL and 81.1 mg/dL, respectively. The mean and standard deviation of ΣPG values of the group of Δ myo-inositol (+) and urinary glucose (+) were 791 mg/dL and 164.8 mg/dL, respectively. Furthermore, as compared with ΣPG of the group of Δ myo-inositol (−) and urinary glucose (−), ΣPG of the group of Δ myo-inositol (+) and urinary glucose (−) was significantly higher, and also ΣPG of the group of Δ myo-inositol (+) and urinary glucose (+) was significantly much higher. These show the degree of impaired glucose tolerance could be determined non-invasively by determining urinary myo-inositol and urinary glucose in combination.

Example 4

Detection of Impaired Early Insulin Secretion by Determination of Urinary myo-Inositol and Urinary Glucose 1) Subjects:
The same as those of Example 1.
2) Reagents and Assays:
The same as those of Example 1.
3) Method:
The same as that of Example 3.
4) Results:
The case showing Δ myo-inositol content of 10 μg/mg Cre or more was referred to as plus (+), while the other case was referred to as minus (−). Likewise for the urinary glucose, the case showing an urinary glucose level of 50 mg/dL or more at 2 hours after glucose load was referred to as "+", while the other case was referred to as "−". The insulinogenic index values calculated in Example 2 were used.

The respective insulinogenic index values (ΔIRI 30-0/ΔPG 30-0) of the group of Δ myo-inositol (−) and urinary glucose (−), the group of Δ myo-inositol (+) and urinary glucose (−), and the group of Δ myo-inositol (+) and urinary glucose (+) were compared with one another.

Figure 8:
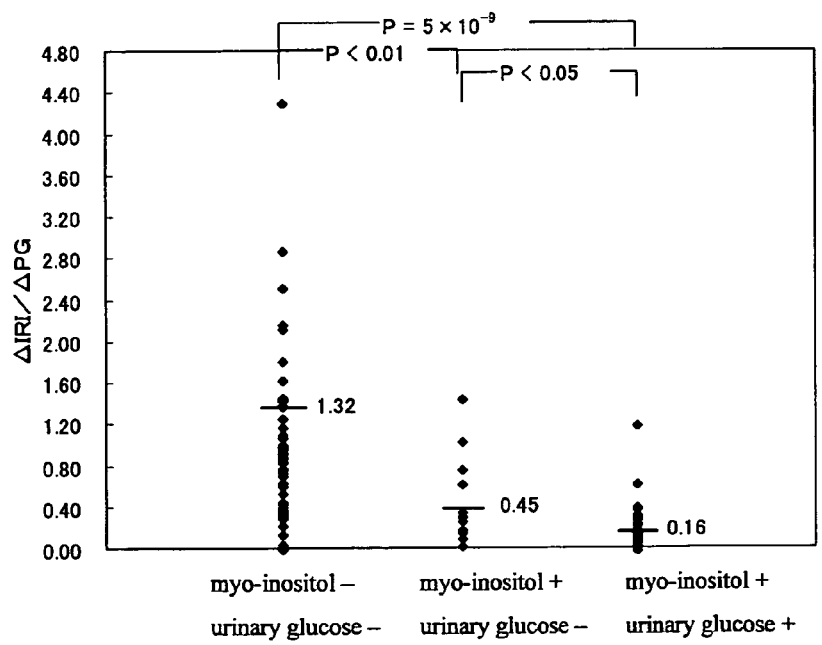
FIG. 8 shows the relationship between each group and insulinogenic index according to Example 4.

The results are shown in FIG. 8. As shown in FIG. 8, the mean and standard deviation of ΔIRI 30-0/ΔPG 30-0 of the group of Δ myo-inositol (−) and urinary glucose (−) were 1.32 and 0.79, respectively. The mean and standard deviation of ΔIRI 30-0/ΔPG 30-0 of the group of Δ myo-inositol (+) and urinary glucose (−) were 0.45 and 0.42, respectively. The mean and standard deviation of ΔIRI 30-0/ΔPG 30-0 of the group of Δ myo-inositol (+) and urinary glucose (+) were 0.16 and 0.19, respectively. Furthermore, as compared with ΔIRI 30-0/ΔPG 30-0 of the group of Δ myo-inositol (−) and urinary glucose (−), ΔIRI 30-0/ΔPG 30-0 of the group of Δ myo-inositol (+) and urinary glucose (−) was significantly lower, and also ΔIRI 30-0/ΔPG 30-0 of the group of Δ myo-inositol (+) and urinary glucose (+) was significantly much lower. These show that the degree of impaired early insulin secretion could be determined non-invasively by determining urinary myo-inositol and urinary glucose in combination.

Example 5

Detection of Mild Impaired Glucose Tolerance by Determination of Urinary myo-Inositol 1) Subjects:

Out of those shown in Example 1, 59 subjects judged as NGT showing the fasting blood glucose level of less than 110 mg/dl and the two-hour postload glucose level of less than 140 mg/dl.

2) Regents and Assays:

The same as those of Example 1.

3) Method:

Out of subjects judged as NGT, those having the one-hour postload glucose level of 180 mg/dL or more or the two-hour postload glucose level of 120 mg/dL or more were referred to as B group or cases showing slightly decreased glucose tolerance (mild impaired glucose tolerance) and the others were referred to as A group. Fifty nine subjects of NGT included 45 subjects of A group and 14 subjects of B group. The myo-inositol content to the amount of urinary creatinine excreted (myo-inositol/creatinine) in A or B group was obtained by determining myo-inositol levels and creatinine levels in each urine sample just before 75 g oral glucose load, and at 60 and 120 minutes after the glucose load.

In addition, Δ myo-inositol content [(myo-inositol content at 60 min−myo-inositol content before load)/2]+[(myo-inositol content at 120 min−myo-inositol content before load)/2] was used as the index of myo-inositol level between before and after the glucose load.

Figure 9:
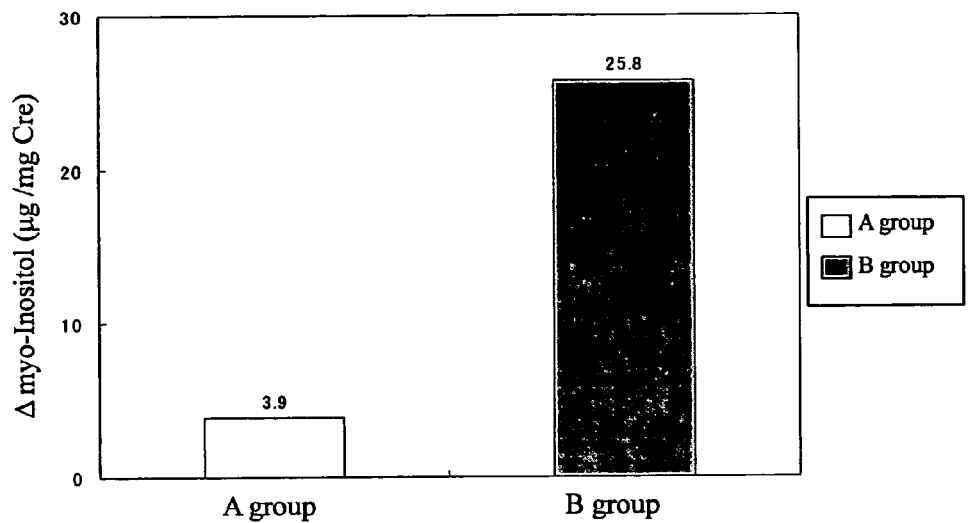
FIG. 9 shows the relationship between each group and myo-inositol level according to Example 5.

4) Results:

The results are shown in FIG. 9. As shown in FIG. 9, the mean of Δ myo-inositol content of A group was 3.9 μg/mg Cre and the mean of Δ myo-inositol content of B group was 25.8 μg/mg Cre. As compared with A group, B group (mild impaired glucose tolerance) with slightly decreased glucose tolerance resulted in higher Δ myo-inositol content.

Example 6

Detection of Insulin Secretory Defect by Determination of Urinary myo-Inositol 1) Subjects:

The same as those of Example 1.

2) Reagents and Assays:

The same as those of Example 1.

3) Method:

Out of subjects judged as NGT, those having the insulinogenic index of less than 0.4 were referred to as B group and the others were referred to as A group. Fifty nine subjects of NGT included 37 subjects of A group and 22 subjects of B group. The myo-inositol content to the amount of urinary creatinine excreted (myo-inositol/creatinine) in A or B group was obtained by determining myo-inositol levels and creatinine levels in each urine sample just before 75 g oral glucose load, and at 60 and 120 minutes after the glucose load.

In addition, Δ myo-inositol content [(myo-inositol content at 60 min−myo-inositol content before load)/2]+[(myo-inositol content at 120 min−myo-inositol content before load)/2] was used as the index of myo-inositol level between before and after the glucose load.

4) Results

Figure 10:
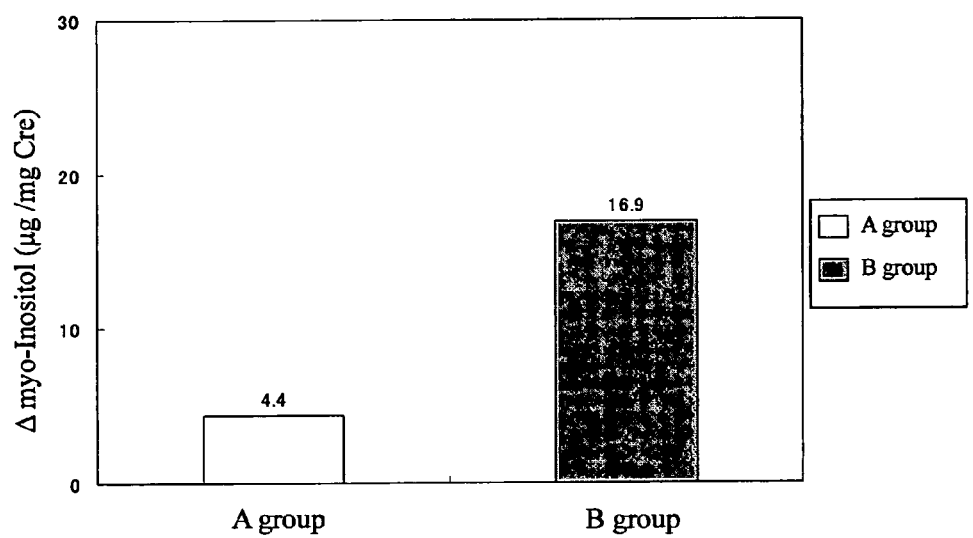
FIG. 10 shows the relationship between each group and myo-inositol level according to Example 6.

The results are shown in FIG. 10. As shown in FIG. 10, the mean of Δ myo-inositol content of A group was 4.4 μg/mg Cre and the mean of Δ myo-inositol content of B group was 16.9 μg/mg Cre. As compared with A group, B group with impaired early insulin secretion resulted in higher Δ myo-inositol content

Example 7

Relationship between Urinary myo-Inositol in Glucose Load Test and Urinary myo-Inositol in Meal Load Test 1) Subjects:

Out of those shown in Example 1, 52 subjects who agreed with taking a meal load test, which included 22 subjects of NGT (C group), 14 subjects of borderline type (B group), and 16 subjects of diabetes meritus (D group). Blood samples were collected before the meal and at 120 minutes after the meal, and then blood glucose level and insulin level were determined. In addition, urine samples were collected before the meal and at 120 minutes after the meal, and then myo-inositol level, urinary glucose level, and creatinine level were determined.

2) Reagent and Assays:

The same as those of Example 1.

3) Method:

After Blood samples and urine samples were collected in fasting condition, the subjects ingested a meal. The meal included retort-packed cooked foods (Wellness Menus (Nichirei Corporation) and packed boiled rice (Sato Foods Industries, Co., Ltd.)) containing 91.6 g carbohydrate, 31.0 g protein, 13.9 g fat, and 1.1 g sodium with 662 kcal energy. At 120 minutes after taking the meal, blood samples and urine samples were collected. The myo-inositol content to the amount of urinary creatinine excreted (myo-inositol/creatinine) was obtained by determining myo-inositol level and creatinine level in each urine sample. In addition, Δ myo-inositol content [(myo-inositol content at 120 min−myo-inositol content before load)] was used as an index of myo-inositol content between before and after the meal.

Figure 11:
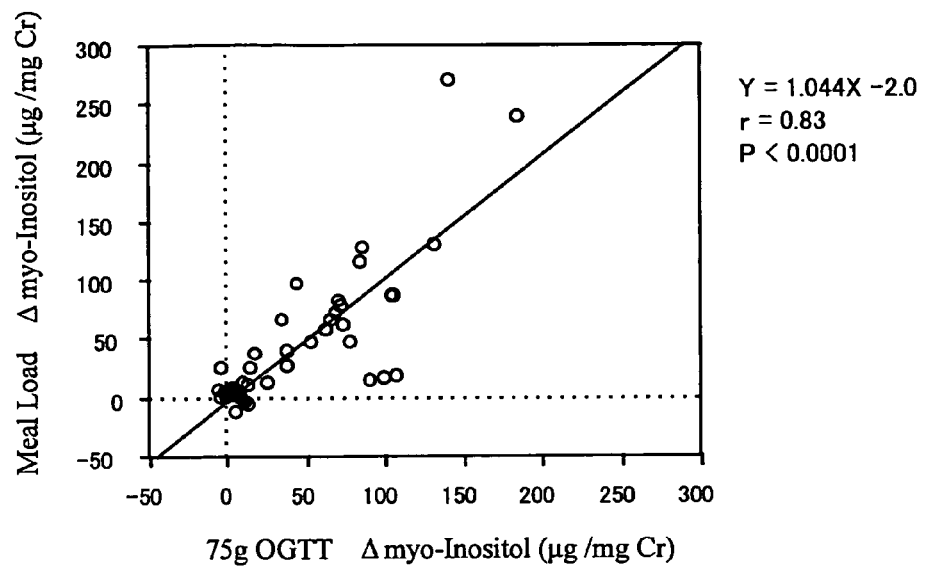
FIG. 11 shows the correlation between urinary myo-inositol levels in the glucose tolerance test and in the meal tolerance test according to Example 7.

4) Results:

FIG. 11 shows the relationship between Δ myo-inositol (X axis) in the glucose load test and Δ myo-inositol (Y axis) in the meal load test. As shown in FIG. 11, Δ myo-inositol in the glucose load test and Δ myo-inositol in the meal load test showed a very good correlation (Y=1.044X−2.0, r=0.83, P<0.0001) and showed almost the same values. These results reveal that mild impaired glucose tolerance or insulin secretory defect can be detected by determining urinary myo-inositol levels before and after a meal, even if the glucose load test is not performed.

Example 8

Relationship between Urinary myo-Inositol in Glucose Load Test and Urinary myo-Inositol in Meal Load Test 1) Subjects:

The same as those of Example 7.

2) Reagents and Assays:

The same as those of Example 1.

3) Method:

The same as that of Example 7.

4) Results

Figure 12:
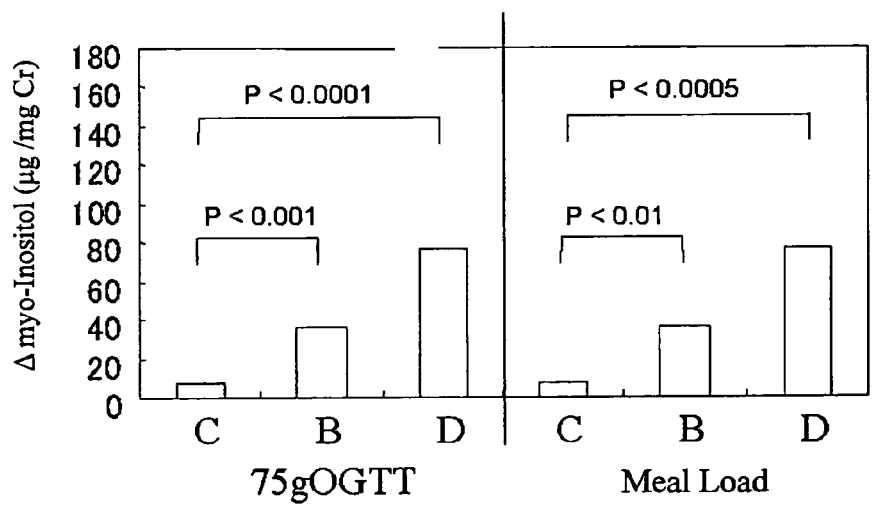
FIG. 12 shows the relationship in each group between Δ myo-inositol in the glucose tolerance test and Δ myo-inositol in the meal tolerance test according to Example 8.

FIG. 12 shows the relationship between Δ myo-inositol in the glucose load test and Δ myo-inositol in the meal load test for each group. As shown in FIG. 12, Δ myo-inositol in the glucose load test and Δ myo-inositol in the meal load test were very well consistent with each other for each group. These results reveal that mild impaired glucose tolerance and insulin secretory defect can be detected by determining urinary myo-inositol levels before and after a meal, even if the glucose load test is not conducted.

Example 9

Figure 13:
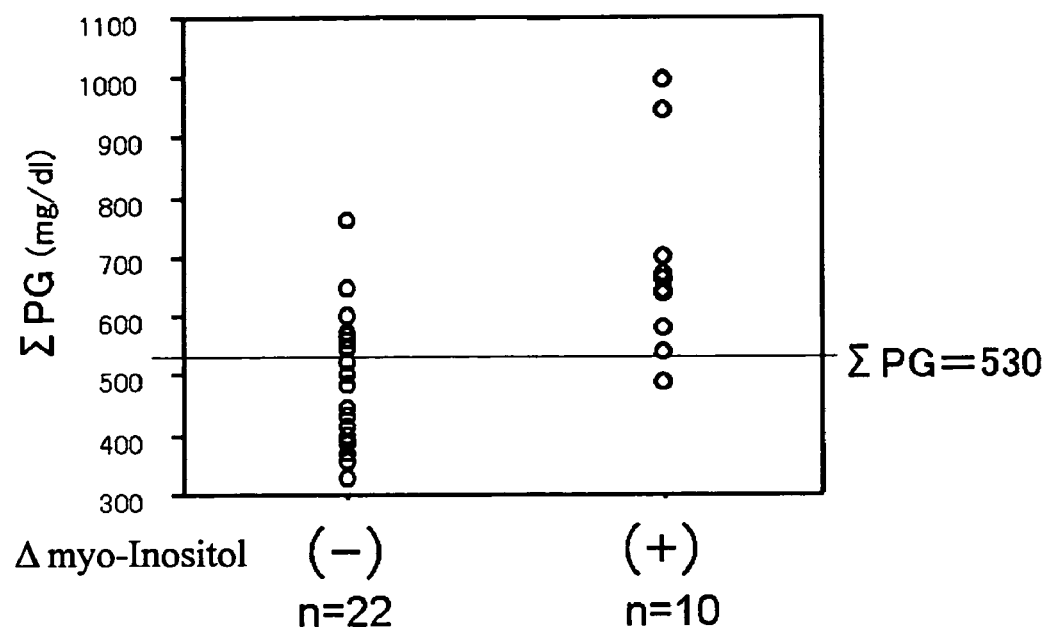
FIG. 13 shows the relationship in urinary glucose negative individuals between urinary myo-inositol level in the meal tolerance test and mild impaired glucose tolerance according to Example 9.

Relationship between Urinary myo-Inositol in Meal Load Test and Mild Impaired Glucose Tolerance in Urinary Glucose Negative Individuals 1) Subjects:
Out of those shown in Example 7, 32 individuals who were negative for urinary glucose (less than 50 mg/dL) at 2 hours after the meal.
2) Reagents and Assays:
The same as those of Example 1.
3) Method:
The same as that of Example 7, except that individuals having Δ myo-inositol of 7 μg/mg Cre or more in the meal load test were referred to as (+) group, and the others were referred to as (−) group.
4) Results:
The results are shown in FIG. 13. As shown in FIG. 13, even in individuals with urinary glucose negative at 2 hours after the meal, many of those of Δ myo-inositol (+) group showed higher ΣPG in the glucose load test, as compared with those of Δ myo-inositol (−) group. These results reveal that, even in individuals with urinary glucose negative at 2 hours after a meal, the degree of impaired glucose tolerance can be determined non-invasively by determining urinary myo-inositol levels before and after a meal.

INDUSTRIAL APPLICABILITY

As described above, the present invention provides a method of detecting mild impaired glucose tolerance and/or impaired early insulin secretion in a non-invasive and convenient manner with good reproducibility.

REFERENCE TO DEPOSITED BIOLOGICAL MATERIAL (1) (a) Name and address of the deposition organization, to which the present biological material has been deposited:
Name: International Patent Organism Depositary, National Institute of Advanced Industrial Science and Technology;
Address: Tsukuba Center 6, 1-1-1 Higashi, Tsukuba, Ibaraki, Japan;
(b) Date of Deposition to Organization of (a):
Oct. 12, 2000 (original deposition date);
(c) Deposit Number for the Deposition given by Organization of (a):
FERM BP-7323.

The invention claimed is:
1. A method of detecting mild impaired glucose tolerance or an insulin secretory defect in a subject, wherein the method comprises:
providing urine samples from said subject, wherein the samples are obtained before and after glucose load, or before and after a meal;
quantitatively determining the myo-inositol level in the samples; and
determining that the subject has mild impaired glucose tolerance or that the subject has an insulin secretory defect based on the concentration of myo-inositol in the samples,
wherein the increment of the concentration of myo-inositol at a characteristic value or higher than a characteristic value of 0 to 20 μg myo-inositol per mg creatinine when measured as an increasing amount of myo-inositol excreted in the urine in a period from 0.5 to 6 hours after 75 g glucose load indicates the subject has mild impaired glucose tolerance or the subject has an insulin secretory defect.
2. The method according to claim 1, wherein the quantitative determination of myo-inositol level in the sample is carried out using an enzyme.
3. The method according to claim 2, wherein the enzyme is myo-inositol dehydrogenase.
4. The method according to claim 2 or 3, wherein the quantitative determination of the myo-inositol level using the enzyme is carried out by an enzymatic cycling method.
5. The method according to claim 1 or 2, wherein the myo-inositol level is quantitatively determined after elimination of sugars other than myo-inositol in the sample.
6. The method according to claim 5, wherein two kinds of kinases are simultaneously used for the reaction of eliminating sugars other than myo-inositol in the sample.
7. The quantitative method according to claim 6, wherein said two kinds of kinases are ATP-hexokinase and ADP-hexokinase.
8. The quantitative method according to claim 2, wherein thio-NAD is used as a coenzyme at a final concentration of 0.1 mM or more in the reaction of quantitatively determining myo-inositol.
9. The quantitative method according to claim 2, wherein thio-NAD is used as a coenzyme at a final concentration of 2 to 10 mM in the reaction of quantitatively determining myo-inositol.
10. The method according to claim 1 or 2, wherein the characteristic value is 8 to 12 μg myo-inositol per mg creatinine when measured as an increasing amount of myo-inositol excreted in the urine after 75 g glucose load.
11. The method according to claim 1 or 2, wherein a glucose level in the sample is quantitatively determined in addition to the myo-inositol level in the sample.
12. The method of detecting mild impaired glucose tolerance or insulin secretory defect according to claim 1 or 2, wherein the myo-inositol level is quantitatively determined after glucose in the sample is eliminated by a method comprising:
reacting ATP with glucose in the sample to convert them to ADP and glucose-6-phosphate; and
reacting the thus obtained ADP with glucose in the sample to convert them to AMP and glucose-6-phosphate.

* * * * *